(12) United States Patent
Ganguli et al.

(10) Patent No.: US 12,091,689 B2
(45) Date of Patent: Sep. 17, 2024

(54) DELIVERY OF THERAPEUTICS IN VIVO VIA A CRISPR-BASED CASCADE SYSTEM

(71) Applicant: VedaBio, Inc., San Diego, CA (US)

(72) Inventors: Anurup Ganguli, San Diego, CA (US); Joshua Miller, San Diego, CA (US); Andrew Garst, San Diego, CA (US); Robert Plasschaert, San Diego, CA (US); Swetha Murali, San Diego, CA (US)

(73) Assignee: VedaBio, Inc., San Diego, CA (US)

( * ) Notice: Subject to any disclaimer, the term of this patent is extended or adjusted under 35 U.S.C. 154(b) by 24 days.

(21) Appl. No.: 18/375,415

(22) Filed: Sep. 29, 2023

(65) Prior Publication Data

US 2024/0110164 A1 Apr. 4, 2024

Related U.S. Application Data

(60) Provisional application No. 63/411,871, filed on Sep. 30, 2022.

(51) Int. Cl.
 *C12N 9/22* (2006.01)

(52) U.S. Cl.
 CPC .......... *C12N 9/22* (2013.01); *C12N 2310/122* (2013.01); *C12N 2310/20* (2017.05)

(58) Field of Classification Search
 CPC .............................. C12N 9/22; C12N 2310/20
 See application file for complete search history.

(56) References Cited

U.S. PATENT DOCUMENTS

| | | |
|---|---|---|
| 10,253,365 B1 | 4/2019 | Doudna et al. |
| 10,266,886 B2 | 4/2019 | Abudayyeh et al. |
| 10,266,887 B2 | 4/2019 | Abudayyeh et al. |
| 10,337,051 B2 | 7/2019 | Doudna et al. |
| 10,494,664 B2 | 12/2019 | Doudna et al. |
| 11,021,740 B2 | 6/2021 | Abudayyeh et al. |
| 11,060,115 B2 | 7/2021 | Severinov et al. |
| 11,104,937 B2 | 8/2021 | Abudayyeh et al. |
| 11,118,224 B2 | 9/2021 | Doudna et al. |
| 11,174,470 B2 | 11/2021 | Harrington et al. |
| 11,174,515 B2 | 11/2021 | Abudayyeh et al. |
| 11,273,442 B1 | 3/2022 | Chen et al. |
| 11,421,250 B2 | 8/2022 | Severinov et al. |
| 11,447,824 B2 | 9/2022 | Doudna et al. |
| 2014/0377748 A1 | 12/2014 | Tan et al. |
| 2016/0040189 A1* | 2/2016 | Kennedy ............. C12N 15/102 252/189 |
| 2016/0083785 A1 | 3/2016 | Bone et al. |
| 2016/0186213 A1* | 6/2016 | Zhang ................... C12N 15/63 800/278 |
| 2018/0023081 A1 | 1/2018 | Hagedorn et al. |
| 2018/0155716 A1 | 6/2018 | Zhang et al. |
| 2018/0282722 A1 | 10/2018 | Jakimo et al. |
| 2019/0112648 A1 | 4/2019 | Schaal et al. |
| 2019/0201550 A1 | 7/2019 | Maeder et al. |
| 2019/0241954 A1 | 8/2019 | Doudna et al. |
| 2019/0256900 A1 | 8/2019 | Zhang et al. |
| 2020/0010879 A1 | 1/2020 | Doudna et al. |
| 2020/0056167 A1 | 2/2020 | Dong et al. |
| 2020/0157611 A1 | 5/2020 | Qi et al. |
| 2020/0165594 A1 | 5/2020 | Zhang et al. |
| 2020/0277600 A1 | 9/2020 | Zhang et al. |
| 2020/0392473 A1 | 12/2020 | Zhang et al. |
| 2021/0102183 A1 | 4/2021 | Cameron et al. |
| 2021/0102242 A1 | 4/2021 | Chen et al. |
| 2021/0108267 A1 | 4/2021 | Zhang et al. |
| 2021/0163944 A1 | 6/2021 | Zhang et al. |
| 2021/0166783 A1 | 6/2021 | Shmakov et al. |
| 2021/0269866 A1 | 9/2021 | Zhang et al. |
| 2021/0317527 A1 | 10/2021 | Doudna et al. |
| 2021/0388437 A1 | 12/2021 | Doudna et al. |
| 2022/0025463 A1 | 1/2022 | Abudayyeh et al. |
| 2022/0333208 A1 | 10/2022 | Gootenberg et al. |
| 2023/0193368 A1 | 6/2023 | Rananaware et al. |

FOREIGN PATENT DOCUMENTS

| | | |
|---|---|---|
| CN | 114058679 A | 2/2022 |
| CN | 114262730 A | 4/2022 |
| WO | WO 2014/143228 A1 | 9/2014 |
| WO | WO 2016/201138 A1 | 12/2016 |
| WO | WO 2020/191248 | 9/2020 |
| WO | WO 2020/191376 | 9/2020 |
| WO | WO 2021/021532 A1 | 2/2021 |
| WO | WO 2021/108717 A2 | 6/2021 |
| WO | WO 2021/146534 A1 | 7/2021 |
| WO | WO 2021/236651 A1 | 11/2021 |
| WO | WO 2022/061166 A1 | 3/2022 |

(Continued)

OTHER PUBLICATIONS

Aman et al., Nucleic Acid Detection Using CRISPR/Cas Biosensing Technologies. ACS Synth. Biol. 2020, 9, 1226-1233 (Year: 2020).*

(Continued)

*Primary Examiner* — Celine X Qian
*Assistant Examiner* — Tiffany Nicole Grooms
(74) *Attorney, Agent, or Firm* — Sarah Brashears

(57) ABSTRACT

The present disclosure relates to compositions of matter and methods used to activate effector nucleic acids and effector targets in vivo via a CRISPR-based cascade system. The compositions and methods achieve non-specific delivery of cascade system components to cells yet the cascade system works in a cell-specific manner.

30 Claims, 27 Drawing Sheets

(56) References Cited

FOREIGN PATENT DOCUMENTS

| WO | WO 2022/133108 A2 | 6/2022 |
| --- | --- | --- |
| WO | WO 2022/266513 A2 | 12/2022 |
| WO | WO 2023/278629 A1 | 1/2023 |
| WO | WO 2023/287669 A2 | 1/2023 |
| WO | WO 2023/015259 A2 | 2/2023 |
| WO | WO 2023/056451 A1 | 4/2023 |
| WO | WO 2023/081902 A1 | 5/2023 |
| WO | WO 2023/114052 A1 | 6/2023 |
| WO | WO 2023/114090 A2 | 6/2023 |

OTHER PUBLICATIONS

Koonin et al. 2017. Diversity, classification and evolution of CRISPR-Cas systems. Current Opinion in Microbiology, 37-67-78 (Year: 2017).*

Li, SY., Cheng, QX., Liu, JK. et al. CRISPR-Cas12a has both cis- and trans-cleavage activities on single-stranded DNA. Cell Res 28, 491-493 (2018). https://doi.org/10.1038/s41422-018-0022-x (Year: 2018).*

Li, et al., "Applying CRISPR-Cas12a as Signal Amplifier to Construct Biosensors for Non-DNA Targets in Ultra-low Concentrations", ACS Sensors, doi: 10.1021/acssensors.9b02305, pp. 1-23, Mar. 12, 2020.

Kim, et al., "Chimeric crRNAs with 19 DNA residues in the guide region show retained DNA cleavage activity of Cas9 with a potential to improve the specificity", The Royal Society of Chemistry, pp. 1-16, 2019.

Kim, et al., "Enhancement of target specificity of CRISPR-Cas12a by using a chimeric DNA-RNA guide", Nucleic Acids Research, doi: 10.1093/nar/gkaa605, vol. 48, No. 15, pp. 8601-8616, Jul. 20, 2020.

Swarts, et al., "Mechanistic Insights into the Cis- and Trans-acting Deoxyribonuclease Activities of Cas12a", Mol Cell, doi: 10.1016/j.molcel.2018.11.021, pp. 1-28, Feb. 7, 2019.

Nguyen, et al., "Enhancement of trans-cleavage activity of Cas12a with engineered crRNA enables amplified nucleic acid detection", Nature Communications, doi: 10.1038/s41467-020-18615-1, pp. 1-13, 2020.

Ooi, et al., "An engineered CRISPR-Cas12a variant and DNA-RNA hybrid guides enable robust and rapid COVID-10 testing", Nature Communications, doi: 10.1038/s41467-021-21996-6, pp. 1-23, 2021.

Shi, et al., "A CRISPR-Cas autocatalysis-driven feedback amplification network for supersensitive DNA diagnostics", Science Advances, doi: 10.1126/sciadv.abc7802, pp. 1-9, Jan. 27, 2021.

The Board of Trustees of the University of Illinois, "CRISPR Cascade", International PCT Application No. PCT/US22/33985, filed Jun. 17, 2022.

Chen, et al., "CRISPR-Cas12a target binding unleashes indiscriminate single-stranded DNase activity", Howard Hughes Medical Institute, Science, 360(6387), pp. 436-439, Apr. 27, 2018.

Liu, et al., "Accelerated RNA detection using tandem CRISPR nucleases", Nature Chemical Biology, vol. 17, doi: 10.1038/s41589-021-0084202, pp. 982-988, Sep. 2021.

Gootenberg, et al., "Nucleic acid detection with CRISPR-Cas13a/C2c2", Science, doi:10.1126/science.aam9321, pp. 438-442, Apr. 28, 2017.

Fozouni, et al., "Amplification-free detection of SARS-CoV-2 with CRISPR-Cas13a and mobile phone microscopy", Cell, doi.org/10.1016/j.cell.2020.12.001, pp. 323-333, Jan. 21, 2021.

Kaminski, et al., "CRISPR-based diagnostics", Nature Biomedical Engineering, vol. 5, doi.org/10.1038/s41551-021-00760-7, pp. 643-656, Jul. 2021.

Zhou, et al., "CRISPR/Cas13a Powered Portable Electrochemiluminescence Chip for Ultrasensitive and Specific MiRNA Detection", Advanced Science News, doi: 10.1002/advs.201903661, pp. 1-10, 2020.

Zhao, et al., "CRISPR-Cas13a system: A novel tool for molecular diagnostics", Frontiers in Microbiology, doi:10.3389/fmicb.2022.1060947, pp. 1-18, Dec. 8, 2022.

Zhou, et al., "A Decade of CRISPR Gene Editing in China and Beyond: A Scientometric Landscape", The CRISPR Journal, vol. 4, No. 3, doi:10.1089/crispr.2020.0148, pp. 313-320, 2021.

Shinoda, et al., "Automated amplification-free digital RNA detection platform for rapid and sensitive SARS-CoV-2 diagnosis", Communications Biology, doi.org/10.1038/s42003-022-03433-6, pp. 1-8, May 26, 2022.

Gupta, et al., "Cas13d: A New Molecular Scissor for Transcriptome Engineering", Frontiers in Cell and Developmental Biology, vol. 10, doi:10.3389/fcell.2022.866800, pp. 1-22, Mar. 31, 2022.

Schunder, et al., "First indication for a functional CRISPR/Cas system in Francisella tularensis", International Journal of Medical Microbiology, vol. 303, Issue 2, doi:10.1016/j.ijmm.2012.11.004, pp. 1-29, Mar. 2013.

Sha, et al., "Cascade CRISPR/cas enables amplification-free microRNA sensing with fM-sensitivity and single-base-specificity", ChemComm, doi:10.1039/d0cc06412b, pp. 247-250 and 1-15, 2021.

Yang, et al., "Engineered LwaCas13a with enhanced collateral activity for nucleic acid detection", Nature Chemical Biology, vol. 19, doi: 10.1038/s41589-022-01135-y, pp. 45-54, Jan. 2023.

East-Seletsky, et al., "RNA targeting by functionally orthogonal Type VI-A CRISPR-Cas enzymes", Howard Hughes Medical Institute, Mol Cell, pp. 373-383, May 4, 2017.

Schmidt, et al., "Application of locked nucleic acids to improve aptamer in vivo stability and targeting function", Nucleic Acids Research, vol. 32, No. 19, doi:10.1093/nar/gkh862, pp. 5757-5765, Oct. 27, 2004.

Makarova, et al., "Evolutionary classification of CRISPR-Cas systems: a burst of class 2 and derived variants", Nature Reviews | Microbiology, vol. 18, pp. 67-83, Feb. 2020.

Gleditzsch, et al., "PAM identification by CRISPR-Cas effector complexes: diversified mechanisms and structures", RNA Biology, vol. 16, No. 4, doi.org/10.1080/15476286.2018.1504546, pp. 504-517, Jul. 20, 2018.

Kellner, et al., "Sherlock: Nucleic acid detection with CRISPR nucleases", Nat Protoc., doi:10.1038/s41596-019-0210-2, pp. 2986-3012, Oct. 2019.

Liu, et al., "Directed Evolution of CRISPR/Cas Systems for Precise Gene Editing", Trends in Biotechnology, vol. 39, No. 3, Mar. 2021, p. 262-273.

International Search Report and Written Opinion for International Application No. PCT/US2022/036610, dated Jun. 29, 2023, p. 1-93.

International Search Report and Written Opinion for International Application No. PCT/US22/52320, dated Jun. 15, 2023, p. 1-46.

International Search Report and Written Opinion for International Application No. PCT/US2022/052032, dated Apr. 18, 2023, p. 1-19.

Zhang, et al, "An aM-level cascade CRISPR-Dx system (ASCas) for rapid detection of RNA without pre-amplification", Biosensors and Bioelectronics, doi:10.1016/j.bios.2023.115248, Mar. 28, 2023, p. 1-5.

Zeng, et al., "Rapid RNA detection through intra-enzyme chain replacement-promoted Cas13a cascade cyclic reaction without amplification", Analytica Chimica Acta, doi:10.1016/j.aca.2022.340009, May 31, 2022, p. 1-10.

Collias, et al., "CRISPR technologies and the search for the PAM-free nuclease", Nature Communications, doi: 10.1038/s41467-020-20633-y, 2021, p. 1-12.

Huyke, et al., "Enzyme Kinetics and Detector Sensitivity Determine Limits of Detection of Amplification-Free CRISPR-Cas12 and CRISPR-Cas13 Diagnostics", Analytical Chemistry, doi:10.1021/acs.analchem.2601670, Jun. 27, 2022, p. 9826-9834.

Mullally, et al., "5' modifications to CRISPR-Cas9 gRNA can change the dynamics and size of R-loops and inhibit DNA cleavage", Nucleic Acids Research, DOI:10.1093/nar/gkaa477, Jun. 2020, vol. 48, No. 12, p. 6811-6823.

Hong, et al., "Comparison and optimization of CRISPR/dCas9/gRNA genome-labeling systems for live cell imaging", Genome Biology, DOI: 10.1186/s13059-018-1413-5, 2018, p. 7-8.

(56) References Cited

OTHER PUBLICATIONS

Li, et al., "CRISPR-Cas 12a has both cis- and trans-cleavage activities on single-stranded DNA", Cell Research, DOI: 10.1038/s41422-018-0022-x, Feb. 5, 2018, p. 1-3.

Dong, et al., "An anti-CRISPR protein disables type V Cas12a by acetylation", PubMed, DOI:10.1038/s41594-019-0206-1, Feb. 28, 2023, p. 1-1.

Coehlo, et al., "CRISPR Guard protects off-target sites from Cas9 nuclease activity using short guide RNAs", Nature Communications, DOI: 10.1038/s41467-020-17952-5, Aug. 17, 2020, p. 1-12.

* cited by examiner

Loss-Less signal transduction cascade using a combination guide nucleic acid and amplifier molecules

V2 paired guides with single bulge have in vivo editing activity

Cas13 KRAS knockdown

Cas12 HPRT1 editing

\* = RNP1 enhances RNP2 editing

DELIVERY OF THERAPEUTICS IN VIVO VIA A CRISPR-BASED CASCADE SYSTEM

RELATED APPLICATIONS

This application claims priority to U.S. Ser. No. 63/411,871, filed 30 Sep. 2022; and is incorporated by reference in its entirety.

FIELD OF THE INVENTION

The present disclosure relates to compositions of matter and methods used to activate effector nucleic acids and effector targets in vivo via a CRISPR-based cascade system. The compositions and methods achieve non-specific delivery of cascade system components to cells yet the cascade system works in a cell-specific manner.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The holy grail of biotherapeutics has been to develop systems that allow delivery of therapeutic components in a non-specific manner, but to also have the therapeutic components function in a cell-specific manner; that is, for the therapeutic components to work only in cells that require treatment. Non-specific delivery of the therapeutic components alleviates the need for complex cell-targeting systems, and action only in specific cells overcomes the problems associated with aspecific toxic effects of delivery to unaffected cells and tissues.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides compositions of matter and methods to selectively activate an effector nucleic acid (i.e., "effector molecule" or "effector") via a CRISPR-based signal transduction cascade in cells in vivo. The compositions of matter include a first ribonucleoprotein complex (RNP) comprising a first nucleic acid-guided nuclease and a combination guide nucleic acid. The first nucleic acid-guided nuclease can be any nucleic acid-guided nuclease that exhibits trans-cleavage activity. The combination guide nucleic acid couples two guide nucleic acids (i.e., gRNAs), where the first guide nucleic acid is specific for a target nucleic acid of interest in a cell and the second guide nucleic acid is specific for an effector nucleic acid in the cell. The effector nucleic acid may be, e.g., a nucleic acid molecule to be transcribed or translated, a nucleic acid molecule to be edited, a nucleic acid to be knocked out, a repressor to prevent transcription, or an enhancer to enhance transcription.

Thus, there is provided in certain embodiments a method for activating an effector nucleic acid in vivo in a cell comprising the steps of: providing cascade system components to a cell, wherein the cascade system components comprise: a first ribonucleoprotein complex comprising a first nucleic acid-guided nuclease, wherein the first nucleic acid-guided nuclease exhibits both cis- and trans-cleavage activity and a combination guide nucleic acid, wherein the combination guide nucleic acid comprises 1) a first guide nucleic acid portion comprising a region that binds to the first nucleic acid-guided nuclease and a region complementary to a target nucleic acid of interest coupled by a linker to 2) a blocked second guide nucleic acid portion comprising a region that binds to a second nucleic acid-guided nuclease and a region complementary to an effector nucleic acid, wherein the blocked second guide nucleic acid portion initially is blocked and unable to bind the effector nucleic acid or form a second ribonucleoprotein complex with the second nucleic acid-guided nuclease, and wherein the second guide nucleic acid portion when unblocked is able to form the second ribonucleoprotein complex with the second guide nucleic acid-guided nuclease; the second nucleic acid-guided nuclease, wherein the second nucleic acid-guided nuclease exhibits both cis- and trans-cleavage activity; and delivering the cascade system components to cells under conditions that allow the target nucleic acid of interest in the cell, if present, to bind to the first ribonucleoprotein complex, wherein upon binding of the target nucleic acid of interest to the first ribonucleoprotein complex, the first ribonucleoprotein complex becomes active initiating trans-cleavage activity thereby unblocking the blocked second guide nucleic acid portion of the combination guide nucleic acid thereby producing at least one unblocked second guide nucleic acid, and wherein the at least one unblocked second guide nucleic acid molecule forms the second ribonucleoprotein complex with the second nucleic acid-guided nuclease and is able to bind to and activate the effector nucleic acid.

In certain aspects, the first nucleic acid-guided nuclease and the second nucleic acid-guided nuclease are different nucleic acid-guided nucleases, and in some aspects, the first nucleic acid-guided nuclease is an RNA-guided RNA endonuclease and the second nucleic acid-guided nuclease is an RNA-guided DNA endonuclease, whereas in other aspects, the first nucleic acid-guided nuclease is an RNA-guided DNA endonuclease and the second nucleic acid-guided nuclease is an RNA-guided RNA endonuclease. In other exemplary aspects, the first nucleic acid-guided nuclease and the second nucleic acid-guided nuclease are the same nucleic acid-guided nucleases, where the first and second nucleic acid-guided nucleases are RNA-guided RNA endonucleases, or the first and second nucleic acid-guided nucleases are RNA-guided DNA endonucleases. In certain aspects, the first nucleic acid-guided nuclease is a Type V nucleic acid-guided nuclease or a Type VI nucleic acid-guided nuclease.

In some certain exemplary aspects, the blocked second guide nucleic acid portion of the combination guide nucleic acid molecule comprises regions of complementarity to the region complementary to the effector nucleic acid forming clamp sequences and regions of non-complementarity to the region complementary to the effector nucleic acid, wherein at least one of the regions of non-complementarity forms at least one loop. In some aspects, the at least one loop comprises 3-10 nucleotides. In other exemplary aspects, the regions of non-complementarity form two loops, and at least one of the two loops comprises 3 nucleotides, 4 nucleotides. 5, nucleotides, 6 nucleotides, 7 nucleotides, 8 nucleotides, 9 nucleotides, or 10 nucleotides. In some aspects, the regions of non-complementarity form three loops, and in some aspects, at least one of the three loops comprises 3 nucleotides, 4 nucleotides. 5, nucleotides, 6 nucleotides, 7 nucleotides, 8 nucleotides, 9 nucleotides, or 10 nucleotides.

In certain aspects, the method comprises at least two different combination guide nucleic acid molecules, wherein different combination guide nucleic acid molecules comprise different first guide nucleic acid portions that detect different target nucleic acids of interest and wherein different combination guide nucleic acid portions comprise different second guide nucleic acid sequences that activate different effector nucleic acids; in yet other aspects, the method comprises at least two different combination guide nucleic acid molecules, wherein different combination guide nucleic acid molecules comprise different first guide nucleic acid portions that detect different target nucleic acids of interest and wherein different combination guide nucleic acid portions comprise the same second guide nucleic acid sequences that the activate same effector nucleic acids.

In some aspects, the blocked second guide nucleic acid comprises a structure selected from Formulas I-IV. In certain exemplary aspects, the first guide nucleic acid portion of the combination guide nucleic acid is approximately 63 to 70 nucleotides in length. In certain embodiments, the linker of the combination guide nucleic acid is approximately 5-50 nucleotides in length, or approximately 10-40 nucleotides in length, or approximately 10-20 nucleotides in length, and in some aspects, the linker of the combination guide nucleic acid is single-stranded.

In certain aspects, the cascade system components further comprise an amplifier molecule, where in some aspects, the amplifier molecule comprises a blocked target nucleic acid of interest covalently linked to a copy of the blocked second guide nucleic acid portion. In certain aspects, the copy of the blocked second guide nucleic acid portion of the amplifier molecule comprises: regions of complementarity to the region complementary to the effector nucleic acid forming clamp sequences and regions of non-complementarity to the region complementary to the effector nucleic acid, wherein at least one of the regions of non-complementarity forms at least one loop. In some embodiments, the at least one loop comprises 3-10 nucleotides. In other exemplary aspects, the regions of non-complementarity form two loops, and at least one of the two loops comprises 3 nucleotides, 4 nucleotides. 5, nucleotides, 6 nucleotides, 7 nucleotides, 8 nucleotides, 9 nucleotides, or 10 nucleotides. In some aspects, the regions of non-complementarity form three loops, and in some aspects, at least one of the three loops comprises 3 nucleotides, 4 nucleotides. 5, nucleotides, 6 nucleotides, 7 nucleotides, 8 nucleotides, 9 nucleotides, or 10 nucleotides.

Other exemplary embodiments provide a method for activating an effector nucleic acid in vivo in a cell comprising the steps of: providing cascade system components to a cell, wherein the cascade system components comprise: a first ribonucleoprotein complex comprising a first nucleic acid-guided nuclease, wherein the first nucleic acid-guided nuclease exhibits both cis- and trans-cleavage activity and a combination guide nucleic acid, wherein the combination guide nucleic acid comprises 1) a first guide nucleic acid portion comprising a region that binds to the first nucleic acid-guided nuclease and a region complementary to a target nucleic acid of interest coupled by a linker to 2) a blocked second guide nucleic acid portion comprising a region that binds to a second nucleic acid-guided nuclease and a region complementary to an effector nucleic acid, wherein the blocked second guide nucleic acid portion initially is blocked and unable to bind the effector nucleic acid or form a second ribonucleoprotein complex with the second nucleic acid-guided nuclease, and wherein the second guide nucleic acid portion when unblocked is able to form the second ribonucleoprotein complex with the second guide nucleic acid-guided nuclease; the second nucleic acid-guided nuclease, wherein the second nucleic acid-guided nuclease exhibits both cis- and trans-cleavage activity; and an amplifier molecule comprising a blocked target nucleic acid of interest covalently linked to a copy of the blocked second guide nucleic acid portion; and delivering the cascade system components to cells under conditions that allow the target nucleic acid of interest in the cell, if present, to bind to the first ribonucleoprotein complex, wherein upon binding of the target nucleic acid of interest to the first ribonucleoprotein complex, the first ribonucleoprotein complex becomes active initiating trans-cleavage activity thereby unblocking the blocked second guide nucleic acid portion of the combination guide nucleic acid thereby producing at least one unblocked second guide nucleic acid, and wherein the at least one unblocked second guide nucleic acid molecule forms the second ribonucleoprotein complex with the second nucleic acid-guided nuclease and is able to bind to and activate the effector nucleic acid.

Yet other exemplary embodiments provide a composition of matter comprising: a first ribonucleoprotein complex comprising a first nucleic acid-guided nuclease, wherein the first nucleic acid-guided nuclease exhibits both cis- and trans-cleavage activity and a combination guide nucleic acid, wherein the combination guide nucleic acid comprises 1) a first guide nucleic acid portion comprising a region that binds to the first nucleic acid-guided nuclease and a region complementary to a target nucleic acid of interest coupled by a linker to 2) a blocked second guide nucleic acid portion comprising a region that binds to a second nucleic acid-guided nuclease and a region complementary to an effector nucleic acid, wherein the blocked second guide nucleic acid portion initially is blocked and unable to bind the effector nucleic acid or form a second ribonucleoprotein complex with the second nucleic acid-guided nuclease, and wherein the second guide nucleic acid portion when unblocked is able to form the second ribonucleoprotein complex with the second guide nucleic acid-guided nuclease; and the second nucleic acid-guided nuclease, wherein the second nucleic acid-guided nuclease exhibits both cis- and trans-cleavage activity.

In some aspects of these embodiments, the first nucleic acid-guided nuclease and the second nucleic acid-guided nuclease are different nucleic acid-guided nucleases, and in some aspects, the first nucleic acid-guided nuclease is an RNA-guided RNA endonuclease and the second nucleic acid-guided nuclease is an RNA-guided DNA endonuclease, where in other aspects, the first nucleic acid-guided nuclease is an RNA-guided DNA endonuclease and the second nucleic acid-guided nuclease is an RNA-guided RNA endonuclease. In certain other aspects, the first nucleic acid-guided nuclease and the second nucleic acid-guided nuclease are the same nucleic acid-guided nucleases, where the first and second nucleic acid-guided nucleases are RNA-guided RNA endonucleases or the first and second nucleic acid-guided nucleases are RNA-guided DNA endonucleases.

In some certain exemplary aspects, the blocked second guide nucleic acid portion of the combination guide nucleic acid molecule comprises regions of complementarity to the region complementary to the effector nucleic acid forming clamp sequences and regions of non-complementarity to the region complementary to the effector nucleic acid, wherein at least one of the regions of non-complementarity forms at least one loop. In some aspects, the at least one loop comprises 3-10 nucleotides. In other exemplary aspects, the regions of non-complementarity form two loops, and at least one of the two loops comprises 3 nucleotides, 4 nucleotides. 5, nucleotides, 6 nucleotides, 7 nucleotides, 8 nucleotides, 9 nucleotides, or 10 nucleotides. In some aspects, the regions of non-complementarity form three loops, and in some aspects, at least one of the three loops comprises 3 nucleotides, 4 nucleotides. 5, nucleotides, 6 nucleotides, 7 nucleotides, 8 nucleotides, 9 nucleotides, or 10 nucleotides.

In certain aspects, the composition of matter comprises at least two different combination guide nucleic acid molecules, wherein different combination guide nucleic acid molecules comprise different first guide nucleic acid portions that detect different target nucleic acids of interest and wherein different combination guide nucleic acid portions comprise different second guide nucleic acid sequences that activate different effector nucleic acids; in yet other aspects, the method comprises at least two different combination guide nucleic acid molecules, wherein different combination guide nucleic acid molecules comprise different first guide nucleic acid portions that detect different target nucleic acids of interest and wherein different combination guide nucleic acid portions comprise the same second guide nucleic acid sequences that the activate same effector nucleic acids.

In some aspects, in the composition of matter, the blocked second guide nucleic acid comprises a structure selected from Formulas I-IV, and in some aspects, the first guide nucleic acid portion of the combination guide nucleic acid is approximately 63 to 70 nucleotides in length. In certain aspects, the linker of the combination guide nucleic acid is approximately 5-50 nucleotides in length, or approximately 10-40 nucleotides in length, or approximately 10-20 nucleotides in length. In some aspects, the linker of the combination guide nucleic acid is single-stranded.

In certain aspects, the composition of matter further comprises an amplifier molecule comprising a blocked target nucleic acid of interest covalently linked to a copy of the blocked second guide nucleic acid portion, where the copy of the blocked second guide nucleic acid portion of the amplifier molecule comprises: regions of complementarity to the region complementary to the effector nucleic acid forming clamp sequences and regions of non-complementarity to the region complementary to the effector nucleic acid, wherein at least one of the regions of non-complementarity forms at least one loop.

Yet another exemplary embodiment comprises a composition of matter comprising a combination guide nucleic acid comprising 1) a first guide nucleic acid portion comprising a region that binds to a first nucleic acid-guided nuclease and a region complementary to a target nucleic acid of interest coupled by a linker to 2) a blocked second guide nucleic acid portion comprising a) a region that binds to a second nucleic acid-guided nuclease, b) a region complementary to an effector nucleic acid, c) regions of complementarity to the region complementary to the effector nucleic acid forming clamp sequences, and d) regions of non-complementarity to the region complementary to the effector nucleic acid, wherein at least one of the regions of non-complementarity forms at least one loop, wherein the blocked second guide nucleic acid portion initially is blocked and unable to bind the effector nucleic acid or form a second ribonucleoprotein complex with the second nucleic acid-guided nuclease, and wherein the second guide nucleic acid portion when unblocked is able to form the second ribonucleoprotein complex with the second guide nucleic acid-guided nuclease and is then able to bind to and activate the effector nucleic acid.

In some aspects, in the composition of matter, the blocked second guide nucleic acid comprises a structure selected from Formulas I-IV, and in some aspects, the first guide nucleic acid portion of the combination guide nucleic acid is approximately 63 to 70 nucleotides in length. In certain aspects, the linker of the combination guide nucleic acid is approximately 5-50 nucleotides in length, or approximately 10-40 nucleotides in length, or approximately 10-20 nucleotides in length. In some aspects, the linker is single-stranded.

In some aspects, the at least one loop comprises 3-10 nucleotides. In other exemplary aspects, the regions of non-complementarity form two loops, and at least one of the two loops comprises 3 nucleotides, 4 nucleotides. 5, nucleotides, 6 nucleotides, 7 nucleotides, 8 nucleotides, 9 nucleotides, or 10 nucleotides. In some aspects, the regions of non-complementarity form three loops, and in some aspects, at least one of the three loops comprises 3 nucleotides, 4 nucleotides. 5, nucleotides, 6 nucleotides, 7 nucleotides, 8 nucleotides, 9 nucleotides, or 10 nucleotides. In certain aspects, there are two loops and the loops are different sizes, in some aspects, there are two loops and the loops are the same size. In some aspects, there are three loops and the loops are all different sizes and in some aspects, there are three loops and at least two of the loops are the same size.

In some aspects of these embodiments, the first nucleic acid-guided nuclease and the second nucleic acid-guided nuclease are different nucleic acid-guided nucleases, and in some aspects, the first nucleic acid-guided nuclease is an RNA-guided RNA endonuclease and the second nucleic acid-guided nuclease is an RNA-guided DNA endonuclease, where in other aspects, the first nucleic acid-guided nuclease is an RNA-guided DNA endonuclease and the second nucleic acid-guided nuclease is an RNA-guided RNA endonuclease. In certain other aspects, the first nucleic acid-guided nuclease and the second nucleic acid-guided nuclease are the same nucleic acid-guided nucleases, where the first and second nucleic acid-guided nucleases are RNA-guided RNA endonucleases or the first and second nucleic acid-guided nucleases are RNA-guided DNA endonucleases. In some aspects, the combination guide molecule further comprises a hairpin loop formed at the end of a clamp sequence.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which.

It should be understood that the drawings are not necessarily to scale, and that like reference numbers refer to like features.

Definitions

Figure 1A:
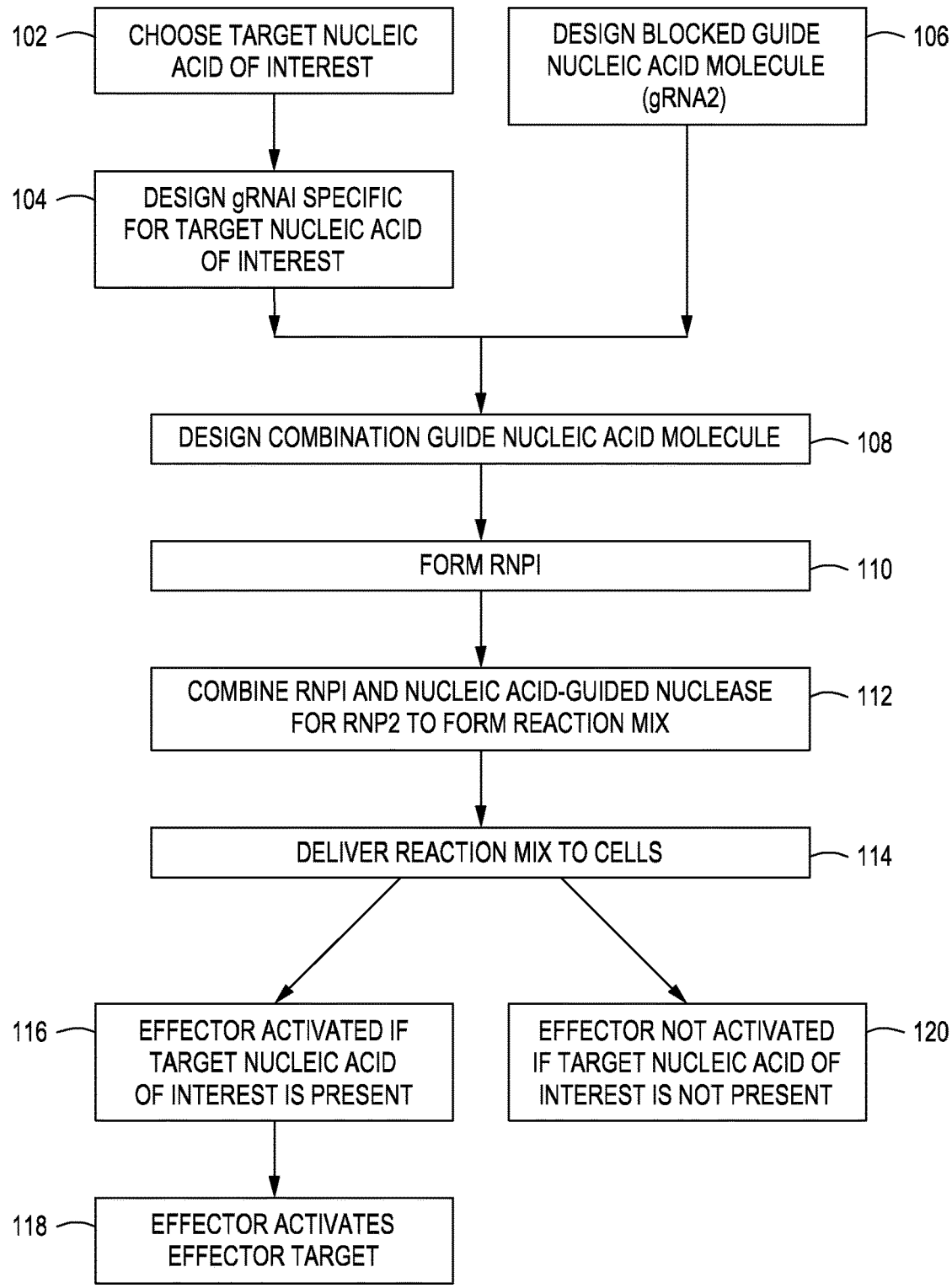
FIG. 1A is a flow chart of one exemplary method disclosed herein for delivering therapeutics in vivo via a CRISPR-based system, according to certain embodiments.

All of the functionalities described in connection with one embodiment of the compositions and/or methods described herein are intended to be applicable to the additional embodiments of the compositions and/or methods except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

Note that as used herein and in the appended claims, the singular forms "a," "an," and "the" include plural referents unless the context clearly dictates otherwise. Thus, for example, reference to "a cell" refers to one or more cells, and reference to "a system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention. Conventional methods are used for the procedures described herein, such as those provided in the art, and demonstrated in the Examples and various general references. Unless otherwise stated, nucleic acid sequences described herein are given, when read from left to right, in the 5' to 3' direction. Nucleic acid sequences may be provided as DNA, as RNA, or a combination of DNA and RNA (e.g., a chimeric nucleic acid).

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

The term "and/or" where used herein is to be taken as specific disclosure of each of the multiple specified features or components with or without another. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

As used herein, the term "about," as applied to one or more values of interest, refers to a value that falls within 10%, 9%, 8%, 7%, 6%, 5%, 4%, 3%, 2%, 1%, or less in either direction (greater than or less than) of a stated reference value, unless otherwise stated or otherwise evident from the context (except where such number would exceed 100% of a possible value).

As used herein, the terms "amplifier molecule" or "amplifier" refer to a construct comprising a blocked target nucleic acid of interest coupled to a blocked second guide nucleic acid (i.e., a blocked gRNA2).

As used herein, the terms "binding affinity" or "dissociation constant" or "$K_d$" refer to the tendency of a molecule to bind (covalently or non-covalently) to a different molecule. A high $K_d$ (which in the context of the present disclosure refers to blocked second guide nucleic acids binding to an effector molecule) indicates the presence of more unbound molecules, and a low $K_d$ (which in the context of the present disclosure refers to unblocked second guide nucleic acids binding to an effector molecule) indicates the presence of more bound molecules.

As used herein, the terms "binding domain" or "binding site" refer to a region on a protein, DNA, or RNA, to which specific molecules and/or ions (ligands) may form a covalent or non-covalent bond. Characteristics of binding sites are chemical specificity, a measure of the types of ligands that will bond, and affinity, which is a measure of the strength of the chemical bond.

As used herein, the terms "blocked guide nucleic acid molecule", "blocked guide molecule", or "blocked second guide nucleic acid molecule" refer to guide nucleic acid molecules (i.e., guide RNAs or gRNAs) that, due to their molecular configuration, cannot form a ribonucleoprotein complex with a nucleic acid-guided nuclease. "Unblocked guide nucleic acid molecule", "unblocked second guide nucleic acid molecule", or "unblocked guide nucleic acid" refer to a formerly blocked guide molecule that can bind to a nucleic acid-guided nuclease to form an RNP complex (i.e., RNP2 in the present context). The unblocked guide nucleic acid has sequence specificity for a desired effector nucleic acid.

The terms "Cas RNA-guided nucleic acid-guided nuclease" or "CRISPR nuclease" or "nucleic acid-guided nuclease" refer to a CRISPR-associated protein that is an RNA-guided nucleic acid-guided nuclease suitable for assembly with a sequence-specific guide RNA to form a ribonucleoprotein (RNP) complex. Type V CRISPR/Cas nucleic acid-guided nucleases are a subtype of Class 2 CRISPR/Cas effector nucleases such as, but not limited to, engineered Cas12a, Cas12b, Cas12c, C2c4, C2c8, C2c5, C2c10, C2c9, CasX (Cas12e), CasY (Cas12d), Cas 13a nucleases or naturally-occurring proteins, such as a Cas12a isolated from, for example, *Francisella tularensis* subsp. *novicida* (Gene ID: 60806594), Candidatus Methanoplasma *termitum* (Gene ID: 24818655), Candidatus Methanomethylophilus alvus (Gene ID: 15139718), and [*Eubacterium*] eligens ATCC 27750 (Gene ID: 41356122), and an artificial polypeptide, such as a chimeric protein.

As used herein, the terms "cis-cleavage", "cis-nucleic acid-guided nuclease activity", "cis-mediated nucleic acid-guided nuclease activity", "cis-cleavage activity", "cis-mediated nuclease activity", and variations thereof refer to sequence-specific cleavage of a target nucleic acid of interest or desired effector nucleic acid by a nucleic acid-guided nuclease in an RNP complex. Cis-cleavage is a single turn-over cleavage event in that only one substrate molecule is cleaved per binding event.

As used herein, the term "combination guide nucleic acid" refers to two guide nucleic acid molecules (i.e., gRNA1 and gRNA2) that are linked together via a linker moiety.

The term "complementary" as used herein refers to Watson-Crick base pairing between nucleotides and specifically refers to nucleotides hydrogen-bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10, or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-ATCGAT-5' is 100% complementary to a region of the nucleotide sequence 5'-GCTAGCTAG-3'.

As used herein, the term "delivering" refers to the placement of two moieties in direct physical association, including in solid or liquid form. Delivering can occur in vivo by administering an agent to a subject.

As used herein, an "effector nucleic acid" or "effector molecule" or "effector" refers to a nucleic acid molecule upon which a ribonucleoprotein complex (here, RNP2) acts to regulate biological activity of a cell.

As used herein, an "effector target" is a molecule in a cell on which an effector nucleic acid acts. An effector target may be a nucleic acid (coding, non-coding or regulatory sequence in genomic or episomal DNA, or the effector nucleic acid itself), a peptide, a lipid, a sugar, a glycoprotein, a small molecule, or the effector target may be any portion of any of these molecules.

The terms "guide nucleic acid" or "guide molecule" or "guide RNA" or "gRNA" refer to a polynucleotide comprising 1) a crRNA region or guide sequence capable of hybridizing to the target strand of a target nucleic acid of interest and 2) a scaffold sequence capable of interacting or complexing with a nucleic acid-guided nuclease. The crRNA region of the gRNA is a customizable component that enables specificity in the nucleic acid-guided nuclease reaction. A guide nucleic acid molecule or gRNA can include any polynucleotide sequence having sufficient complementarity with a target nucleic acid of interest or effector nucleic acid to hybridize with the target nucleic acid of interest or effector nucleic acid and direct sequence-specific binding of a ribonucleoprotein (RNP) complex containing the gRNA and the nucleic acid-guided nuclease to the target nucleic acid or effector nucleic acid. Target nucleic acids of interest and/or effector nucleic acids may include a protospacer adjacent motif (PAM), and, following gRNA binding, the nucleic acid-guided nuclease induces a double-stranded break either inside or outside the protospacer region on the target nucleic acid of interest or effector nucleic acid. A gRNA may contain a spacer sequence including a plurality of bases complementary to a protospacer sequence in the target nucleic acid. For example, a spacer can contain about 2, 3, 4, 5, 6, 7, 8, 9, 10, 11, 12, 13, 14, 15, 20, 25, 30, 35, 40, 45, 50, 55, 60, or more bases. The gRNA spacer may be 50%, 60%, 75%, 80%, 85%, 90%, 95%, 97.5%, 98%, 99%, or more complementary to its corresponding target nucleic acid of interest or effector nucleic acid. Optimal alignment may be determined with the use of any suitable algorithm for aligning sequences. A guide nucleic acid may be from about 20 nucleotides to about 300 nucleotides long. Guide nucleic acids may be produced synthetically or generated from a DNA template.

A "ligand" is a substance that is able to bind to and form a complex with a biomolecule to serve a biological purpose.

"Modified" refers to a changed state or structure of a molecule. Molecules may be modified in many ways including chemically, structurally, and functionally.

As used herein, the terms "preassembled ribonucleoprotein complex", "ribonucleoprotein complex", "RNP complex", or "RNP" refer to a complex containing a guide nucleic acid molecule (gRNA) and a nucleic acid-guided nuclease, where the guide nucleic acid molecule is integrated with the nucleic acid-guided nuclease. The guide nucleic acid molecule, which includes a sequence complementary to a target nucleic acid of interest or effector nucleic acid, guides the RNP to the target nucleic acid of interest or effector nucleic acid and hybridizes to it. The hybridized target nucleic acid or effector nucleic acids are cleaved by the nucleic acid-guided nuclease. In the cascade systems described herein, a first ribonucleoprotein complex (RNP1) includes 1) a combination guide nucleic acid molecule (gRNA) comprising a first guide nucleic acid specific to a target nucleic acid of interest coupled to a blocked second guide nucleic acid specific to an effector nucleic acid, and 2) a first nucleic acid-guided nuclease, such as, for example, Cas12a or Cas14a for a DNA target nucleic acid of interest, or Cas13a for an RNA target nucleic acid of interest. A second ribonucleoprotein complex (RNP2) is formed after the blocked second guide nucleic acid is unblocked and includes the unblocked second guide nucleic acid molecule specific to the effector nucleic acid and a second nucleic acid-guided nuclease, which may be different from or the same as the first nucleic acid-guided nuclease.

As used herein, the terms "protein" and "polypeptide" are used interchangeably. Proteins may or may not be made up entirely of amino acids. As used herein, the term "protein complex" is used to refer to a group of two or more constituent proteins formed by protein-protein interactions that may or may not involve formation of covalent bonds.

The terms "target DNA sequence", "target sequence", "target nucleic acid of interest", "target molecule of interest", "target nucleic acid", or "target of interest" refer to any locus that is recognized by a gRNA sequence in vivo. The "target strand" of a target nucleic acid of interest is the strand of a target nucleic acid of interest that is complementary to a gRNA. A target nucleic acid of interest can include any polynucleotide, such as DNA (ssDNA or dsDNA) or RNA polynucleotides, and may be located in the nucleus or cytoplasm of a cell such as, for example, within an organelle of a eukaryotic cell, such as a mitochondrion or a chloroplast, or it can be exogenous to a host cell, such as a eukaryotic cell or a prokaryotic cell. The target nucleic acid of interest may be associated with a protospacer adjacent motif (PAM) sequence, which may include a 2-5 base pair sequence adjacent to the protospacer. In some embodiments 1, 2, 3, 4, 5, 6, 7, 8, 9, 10, or more target nucleic acids can be detected by the disclosed method.

As used herein, the terms "trans-cleavage", "trans-nucleic acid-guided nuclease activity", "trans-mediated nucleic acid-guided nuclease activity", "trans-cleavage activity", "trans-mediated nuclease activity" and variations thereof refer to indiscriminate, non-sequence-specific cleavage of a nucleic acid molecule by a nucleic acid-guided nuclease (such as by a Cas12, Cas13, and Cas14) which is triggered by a target nucleic acid of interest or an effector nucleic acid binding to an RNP complex. Trans-cleavage is a "multiple turn-over" event, in that more than one substrate molecule is cleaved after initiation by a single turn-over cis-cleavage event.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like.

DETAILED DESCRIPTION

The present disclosure provides compositions of matter and methods to selectively activate one or more effector nucleic acids via a CRISPR-based signal transduction cascade system in cells in vivo. The compositions of matter include a first ribonucleoprotein complex comprising a first nucleic acid-guided nuclease and a combination guide nucleic acid. The combination guide nucleic acid couples two guide nucleic acids (e.g., gRNAs); the first guide nucleic acid comprises a region that binds to a first nucleic acid-guided nuclease and a region specific for a target nucleic acid of interest in a cell, and the second guide nucleic acid (the blocked second guide nucleic acid or blocked guide nucleic acid—that is, only the second guide nucleic acid is blocked and may then be unblocked) comprises a region that binds to a second nucleic acid-guided nuclease and a region specific for an effector nucleic acid in the cell. The target nucleic acid of interest may be any nucleic acid that indicates a biological characteristic or state of a cell and indicates the presence of an effector molecule. The effector nucleic acid may be any nucleic acid that regulates the biological activity of the cell.

The present CRISPR-based cascade system employs a signal transduction mechanism where sensing of a target nucleic acid of interest by a first ribonucleoprotein complex (i.e., RNP1 comprising the combination guide nucleic acid and a first nucleic acid-guided nuclease) triggers creation of the unblocked second guide nucleic acid that can combine with a second nucleic acid-guided nuclease to form a second ribonucleoprotein complex specific for an effector nucleic acid. Because there is a loss in signal transduction in vivo as the trans-cleavage activity of RNP1 acts not only on the second guide nucleic acid but on all nucleic acids present in the cell, the second guide nucleic acid (gRNA2) is coupled to the first guide nucleic acid (gRNA1) to bring the second guide nucleic acid into proximity of RNP1 and the trans-cleavage activity initiated by a target nucleic acid of interest binding to RNP1. That is, the combination guide nucleic acid presented herein is configured to reduce the loss of signal transduction between RNP1 and the second guide nucleic acid (i.e., the unblocked second guide nucleic acid molecule) and hence, RNP2.

FIG. 1A is a flow chart of one exemplary method (100) for effecting in vivo therapeutic transgene activation, according to certain embodiments. In a first step, a target nucleic acid of interest is chosen 102. The target nucleic acid of interest may be any nucleic acid that indicates a biological characteristic or state of a cell, such as, e.g., a gene transcript indicating the presence of a tumor. Further the target nucleic acid of interest is a nucleic acid that indicates the presence of an effector nucleic acid; that is, the target nucleic acid of interest is a proxy for the presence of the effector nucleic acid. Often, the target nucleic acid of interest is a transcript which means that the first nucleic acid-guided nuclease will be, e.g., Cas13a, Cas12g, or other RNA-guided RNA endonuclease. In a next step, a gRNA1 specific for the target nucleic acid of interest is designed 104. In parallel, a blocked second guide nucleic acid is designed 106. Blocked guide nucleic acids, due to their molecular configuration, cannot form a ribonucleoprotein complex with a nucleic acid-guided nuclease. The blocked second guide nucleic acid has complementarity to an effector nucleic acid (also "effector" or "effector molecule"), where "effector" refers to a nucleic acid molecule upon which a ribonucleoprotein complex (here, RNP2) acts to regulate biological activity or activities of a cell.

Once the first guide nucleic acid (i.e., for RNP1) and the blocked guide nucleic acid (i.e., for RNP2) are designed 104, 106, a combination guide nucleic acid molecule is designed 108. The combination guide nucleic acid couples the first guide nucleic acid and the blocked second guide nucleic acid via a linker comprising nucleotides, including modified nucleotides as described infra. Once the combination guide nucleic acid is designed and synthesized, RNP1 can be formed 110 comprising the combination guide nucleic acid and a first nucleic acid-guided nuclease of choice. The first nucleic acid-guided nuclease must exhibit trans-cleavage activity. In alternative embodiments, the combination guide nucleic acid and the first nucleic acid-guided nuclease can be provided to the cells separately rather than providing pre-assembled RNP1s to the cells where the RNP1s are then formed in the cells.

At step 112, the pre-assembled RNP1s are combined with a second nucleic acid-guided nuclease of choice (for RNP2) to form a reaction mix; and at step 114, the reaction mix is delivered to the cells to be treated (e.g., tumor cells, cells infected with a virus, cells comprising a genetic mutation, cells in a particular organ or in a particular location in a subject) or to a subject generally. If the target nucleic acid of interest is present, it will be recognized by RNP1 and cleaved by cis-cleavage activity of RNP1. The trans-cleavage activity initiated by binding of the target nucleic acid of interest to RNP1 will then cleave the blocked second guide nucleic acid to unblock the second guide nucleic acid, where the now unblocked second guide nucleic acid can complex with the second nucleic acid-guided nuclease to form RNP2. RNP2 thus comprises 1) the formerly blocked second guide nucleic acid molecule that has been unblocked; and 2) the second nucleic acid-guided nuclease. Because the unblocked second guide nucleic acid is complementary to the effector nucleic acid, RNP2 recognizes the effector nucleic acid and "activates" the effector nucleic acid 116 by, e.g., editing, knocking out, or otherwise altering the effector nucleic acid. Once the effector is activated 116, the effector may activate an effector target 118 or the effector may serve as both the effector and the effector target. On the other hand, if the target nucleic acid of interest is not present, RNP1 will not be activated, the blocked second guide nucleic acid will not be unblocked and will not form RNP2 with the second nucleic acid-guided nuclease and thus the effector will not activate 120.

Figure 1B:
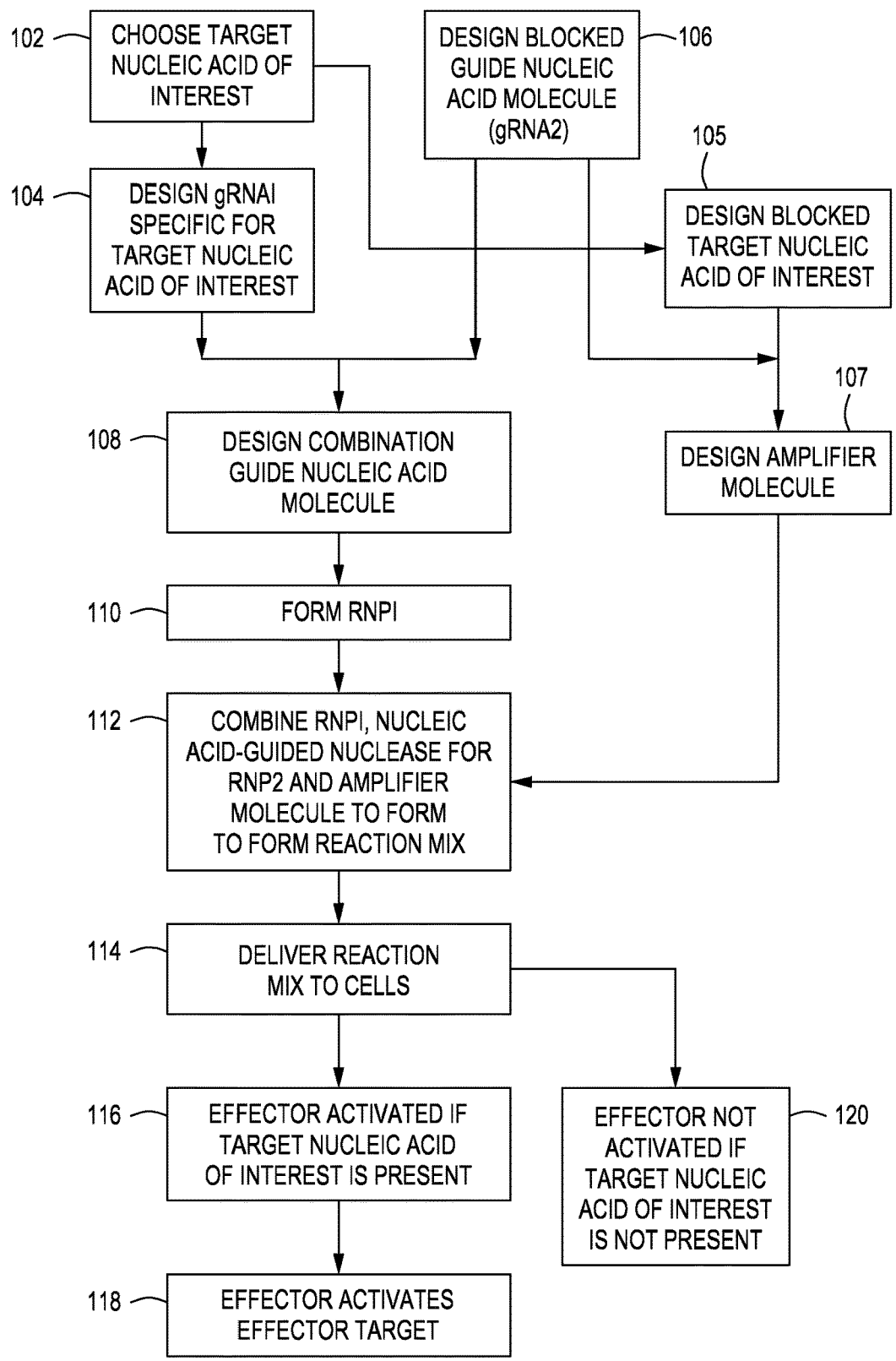
FIG. 1B is a flow chart of an alternative method for delivering effector molecules in vivo via a CRISPR-based cascade system, according to certain embodiments.

FIG. 1B is a flow chart of an alternative method (150) for effecting in vivo therapeutic transgene activation using an amplifier molecule, according to certain embodiments. In a first step, a target nucleic acid of interest is chosen 102. As stated above, the target nucleic acid of interest may be any nucleic acid that indicates a biological characteristic or state of a cell, such as, e.g., a gene transcript indicating the presence of a tumor. Further the target nucleic acid of interest is a nucleic acid that indicates the presence of an effector nucleic acid. In the next step, a gRNA1 comprising a region that binds to a first nucleic acid-guided nuclease and a region specific for the target nucleic acid of interest is designed 104. In addition to designing a gRNA1 for the target nucleic acid of interest 104, a blocked target nucleic acid of interest is designed 105. Blocked target nucleic acids of interest, due to their molecular configuration, cannot combine with the first ribonucleoprotein complexes (RNP1s) to trigger cis- and trans-cleavage by the first nucleic acid-guided nuclease. In addition, a blocked second guide nucleic acid (i.e., gRNA2) is designed 106. Blocked guide nucleic acids, due to their molecular configuration, cannot form a second ribonucleoprotein complex (RNP2) with a nucleic acid-guided nuclease. The blocked second guide nucleic acid has a region that binds to a second nucleic acid-guided nuclease and a region complementary to an effector nucleic acid (also "effector" or "effector molecule"), where "effector" refers to a nucleic acid molecule upon which a ribonucleoprotein complex (here, RNP2) acts to regulate biological activity or activities of a cell.

As with the embodiment shown in FIG. 1A, once the first guide nucleic acid (i.e., for RNP1) and the blocked guide nucleic acid (i.e., for RNP2) are designed 104, 106, a combination guide nucleic acid molecule is designed 108. The combination guide nucleic acid couples the first guide nucleic acid and the blocked second guide nucleic acid via a linker comprising nucleotides, which may include modified nucleotides as described infra. Once the combination guide nucleic acid is designed and synthesized, RNP1 can be formed 110, which comprises the combination guide nucleic acid and a first nucleic acid-guided nuclease of choice. The first nucleic acid-guided nuclease must exhibit trans-cleavage activity. In alternative embodiments, the combination guide nucleic acid and the first nucleic acid-guided nuclease can be provided to the cells separately rather than providing pre-assembled RNP1s to the cells where the RNP1s are then formed in the cells.

In this alternative embodiment, in another step, an amplifier molecule is designed 107. The amplifier molecule couples the blocked target nucleic acid of interest with the blocked second guide nucleic acid molecule. The purpose of the amplifier molecule is to first, supply additional blocked second guide nucleic acid molecules that, when unblocked, can combine with the second nucleic acid-guided nucleases to form second ribonucleoprotein complexes (RNP2s) that can bind and activate additional effector nucleic acids. Second, the amplifier molecule comprises a blocked target nucleic acid of interest that, when unblocked, can combine with additional first ribonucleoprotein complexes (RNP1s) to amplify the trans-cleavage activation of the RNP1s and thus trans-cleavage of additional amplifier molecules and effector nucleic acids.

At step 112, the pre-assembled RNP1s are combined with a second nucleic acid-guided nuclease of choice (for RNP2) and the amplifier molecules to form a reaction mix; and at step 114, the reaction mix is delivered to the cells to be treated (e.g., tumor cells, cells infected with a virus, cells comprising a genetic mutation, cells in a particular organ or in a participation location in a subject) or to a subject generally. If the target nucleic acid of interest is present, it will be recognized by RNP1 and cleaved by cis-cleavage activity of RNP1. The trans-cleavage activity initiated by binding of the target nucleic acid of interest to RNP1 then cleaves the blocked second guide nucleic acid portion of the combination guide nucleic acid molecule and the blocked target nucleic acid of interest and blocked second guide nucleic acid portions of the amplifier molecule, where the now unblocked second guide nucleic acids can complex with the second nucleic acid-guided nucleases to form RNP2s. RNP2 thus comprises 1) the formerly blocked second guide nucleic acid molecules that have been unblocked; and 2) the second nucleic acid-guided nucleases. Because the unblocked second guided nucleic acid is complementary to the effector nucleic acid, RNP2 recognizes the effector nucleic acid and "activates" the effector nucleic acid 116 by, e.g., editing, knocking out, or otherwise altering the effector nucleic acid.

Once the effector is activated 116, the effector may activate an effector target 118 or the effector may serve as both the effector and the effector target. On the other hand, if the target nucleic acid of interest is not present, RNP1 will not be activated, the blocked second guide nucleic acid will not be unblocked and will not form RNP2 with the second nucleic acid-guided nuclease and thus the effector will not activate 120. As for the unblocked target nucleic acid of interest, it is free to combine with and activate another RNP1, which triggers additional trans-cleavage activity from RNP1 and ultimately RNP2.

Note that in the embodiment described in relation to FIG. 1B, there are two "compound" molecules. The first is the "combination guide nucleic acid molecule" or "combination molecule" comprising a first guide nucleic acid (gRNA1) and a blocked second guide nucleic acid (gRNA2). The second is the "amplifier molecule" comprising a blocked target nucleic acid of interest and a blocked second guide nucleic acid (gRNA2). In an alternative embodiment, the amplifier molecule may be employed without the combination molecule; that is, the gRNA1 may be provided to the cell not coupled to blocked gRNA2 but with an amplifier molecule (blocked target nucleic acid of interest+blocked second guide nucleic acid) provided in the reaction mix.

Figure 2:
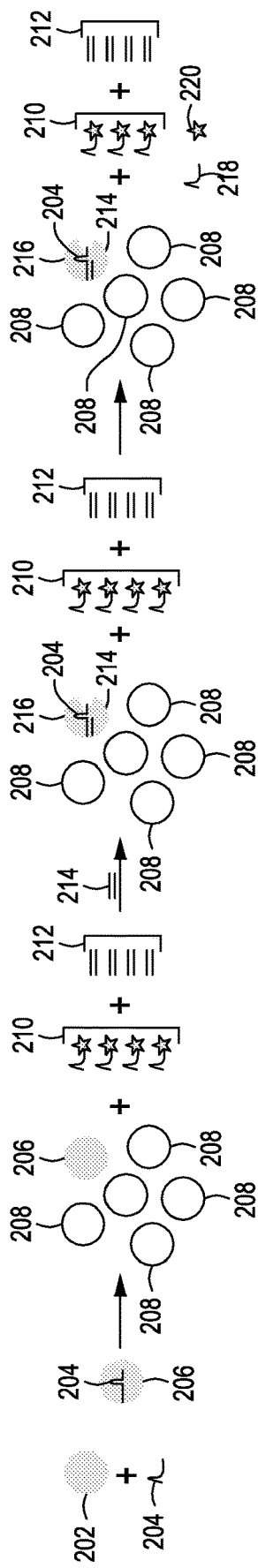
FIG. 2 is a schematic showing detection of a target nucleic acid of interest using a cascade assay mechanism where binding of the target nucleic acid of interest initiates unblocking of blocked second guide nucleic acids and activation of RNP2s, according to certain embodiments.
Figure 2:
Figure 2:
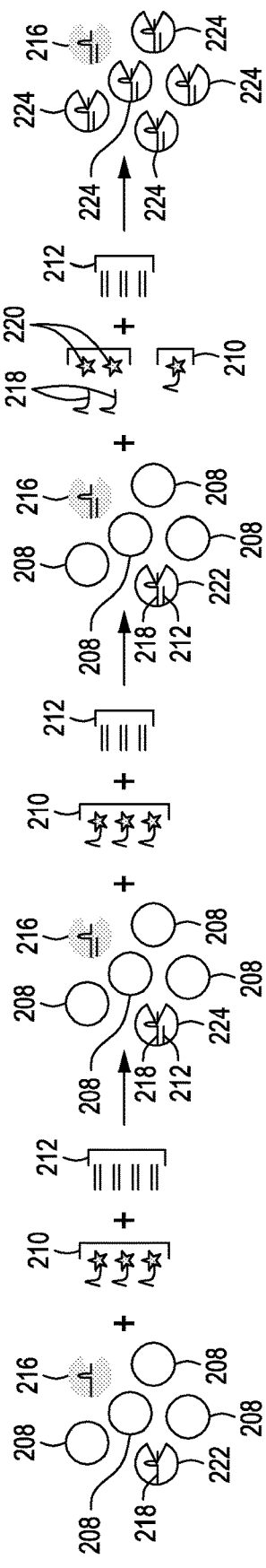
Figure 2:
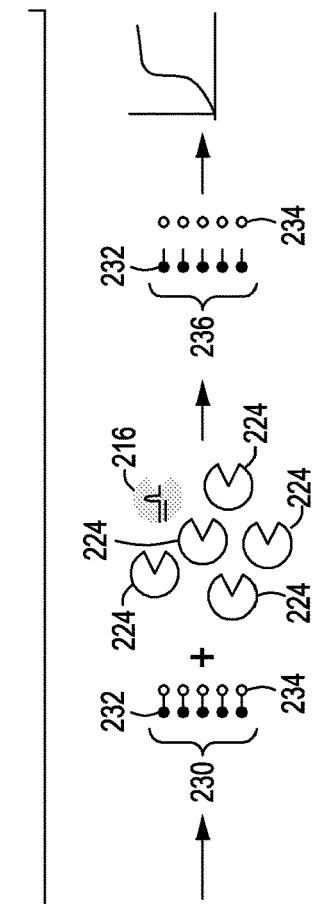

FIG. 2 is a schematic for an in vitro detection assay 200 (such as a diagnostic assay) upon which the CRISPR-based in vivo cascade system described herein is based, according to certain embodiments. The in vitro detection assay 200 uses a two-RNP mechanism, where binding of a target nucleic acid molecule initiates an amplification cascade by converting blocked guide nucleic acid molecules (i.e., high $K_d$ guide nucleic acid molecules) to unblocked guide nucleic acid molecules (i.e., low $K_d$ guide nucleic acid molecules), where "high" and "low" are in relation to the ability to form a ribonucleoprotein complex (i.e., RNP2) with a second nucleic acid-guided nuclease. Step 1 comprises formation of an RNP1 complex 206 comprising a first nucleic acid-guided nuclease 202 and a first guide nucleic acid 204 specific for a target nucleic acid of interest. The RNP1 complex is then combined with a second nucleic acid-guided nuclease 208 (which may be the same nucleic acid-guided nuclease as the first nucleic acid-guided nuclease or may be a different nucleic acid-guided nuclease), blocked guide nucleic acid molecules 210 specific for a signal amplification target (target 2), and copies of the signal amplification target 212 (target 2).

If a target nucleic acid of interest 214 (target 1) is bound by RNP1 206, in step 2, RNP1 216 becomes activated (e.g., 206→216) and cleaves the target nucleic acid of interest 214 via cis-cleavage activity, and trans-cleavage activity is triggered as well. The trans-cleavage activity will cleave at least one of the blocked guide nucleic acids 210 to form an unblocked guide nucleic acid 218 separate from blocking moiety 220 (shown at bottom right of step 2). In step 3, the now unblocked guide nucleic acid 218 combines with the second nucleic acid-guided nuclease 208 to form RNP2 222, which will combine with and cis-cleave at least one of the signal amplification targets 212 (target 2). In addition to cis-cleavage of the signal amplification target 212, the trans-cleavage activity of RNP2 224 is triggered, which in turn cleaves additional signal amplification targets 212, which then combine with more RNP2s 222, triggering more cis- and trans-cleavage of signal amplification targets by RNP2 in a cascade 208 (second nucleic acid-guided nuclease)→222 (RNP2)→224 (activated RNP2)). At the end of the process, all RNP2s 208 will become activated RNP2s 224. For more detail regarding the detection assay shown in FIG. 2, see PCT/US22/33985, filed 17 Jun. 2022.

FIG. 2 at bottom depicts the concurrent activation of reporter moieties. Intact reporter moieties 230 comprise a quencher 232 and a fluorophore 234 linked together by a nucleic acid sequence. The intact reporter moieties 230 are also subject to trans-cleavage by activated RNP1 216 and RNP2 224. The intact reporter moieties 230 become activated reporter moieties 236 when the quencher 232 is separated from the fluorophore 234, thereby emitting a fluorescent signal. Signal strength increases rapidly as more blocked gRNA2s 210 become unblocked gRNA2s 218 triggering cis-cleavage activity of more RNP2s 208 and thus more trans-cleavage activity of the reporter moieties 230.

Figure 3A:
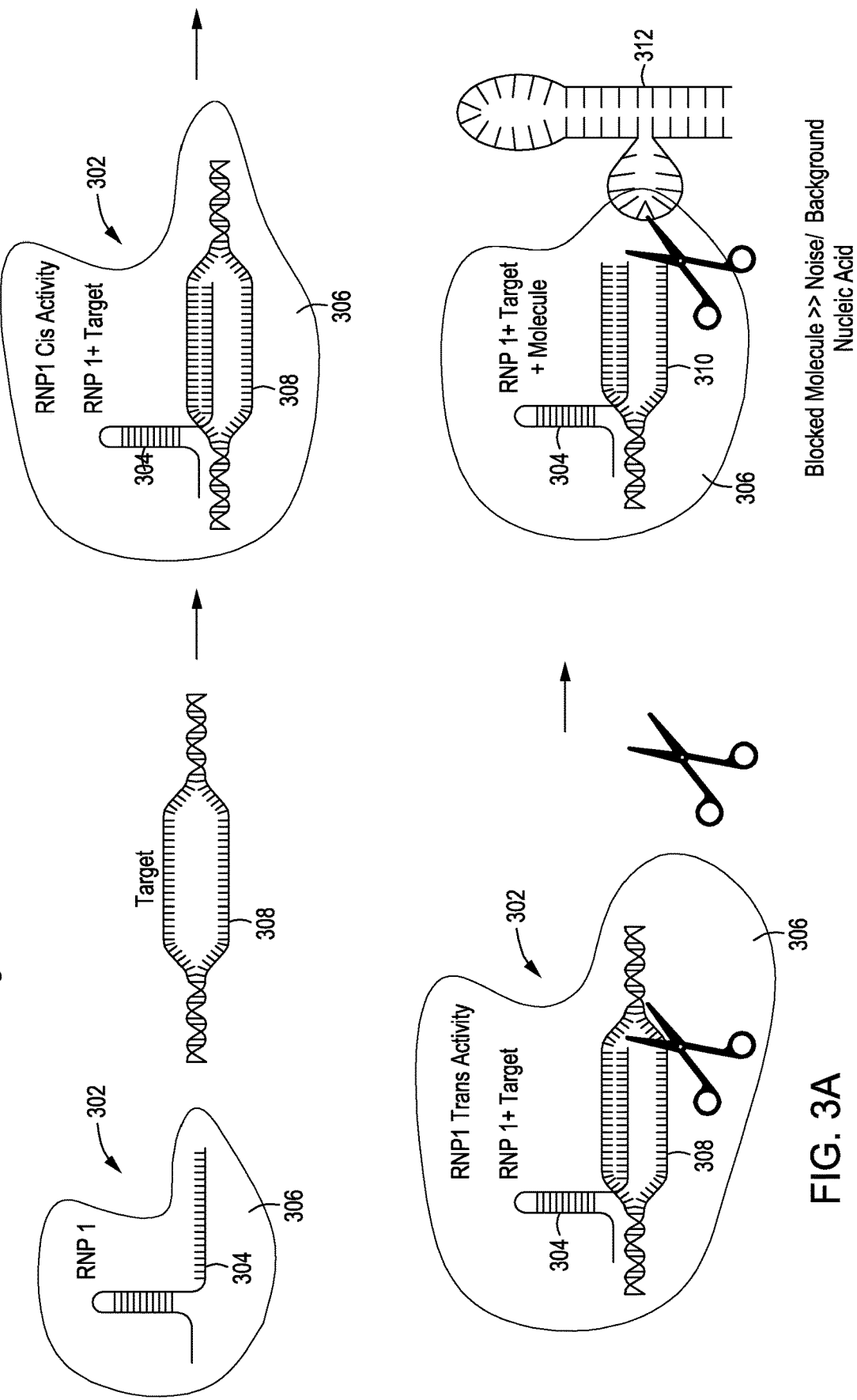
FIG. 3A is a schematic demonstrating signal transduction in an in vitro environment where a blocked second guide nucleic acid can be provided at a controlled concentration and where the concentration of the blocked second guide nucleic acid is much higher than the concentration of other nucleic acids present, according to certain embodiments.

FIG. 3A is a schematic demonstrating signal transduction in an in vitro environment (such as that shown in FIG. 2) where a blocked guide nucleic acid can be provided at a controlled high concentration, according to certain embodiments. FIG. 3A shows RNP1 302 comprising a first nucleic acid-guided nuclease 306 and a guide nucleic acid (gRNA1) 304 which comprises a region that binds to the first nucleic acid-guided nuclease and a region that binds to a target nucleic acid of interest, as well as the target nucleic acid of interest 308. Binding of the target nucleic acid of interest 308 to RNP1 302 cleaves the target nucleic acid of interest 308 and triggers non-specific trans-cleavage activity, indicated by the scissors outside RNP1 302 (bottom left of FIG. 3A). The trans-cleavage activity of RNP1 302 then cleaves at least one blocked second guide nucleic acid 312 (seen as a self-hybridized structure with two loops at bottom right of FIG. 3A) comprising a region that binds to a second nucleic acid-guided nuclease (not shown) and a region complementary to an effector molecule (not shown) thereby freeing the blocked second guide nucleic acid to form a ribonucleoprotein complex (i.e., RNP2, not shown) with the second nucleic acid-guided nuclease (not shown). In this in vitro environment, the concentration of blocked guide nucleic acids can be controlled by providing, e.g., nM concentrations of the blocked guide nucleic acids thus ensuring that the signal transduction from RNP1 302 (trans-cleavage) to unblocking the blocked guide nucleic acid 312 and on to formation of RNP2 (not shown) will take place. For more detailed information on blocked guide nucleic acids see PCT/US22/36610, filed 9 Jul. 2022.

Figure 3B:
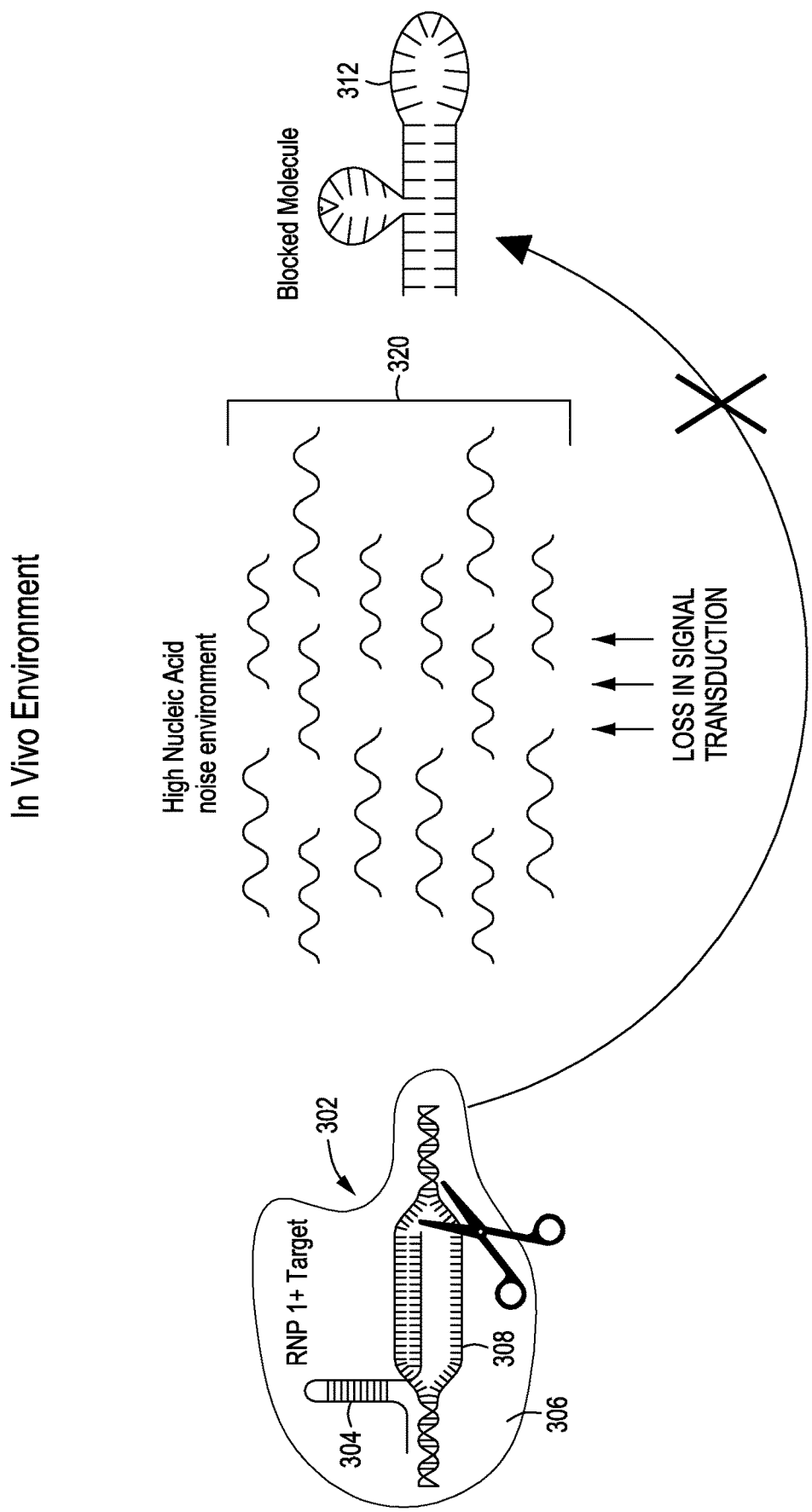
FIG. 3B is a schematic demonstrating signal transduction in an in vivo environment where cellular nucleic acids are present in a high background concentration, according to certain embodiments. In an in vivo environment, it is not practical to provide the blocked second guide nucleic acid at a much higher concentration above the background cellular nucleic acids.

FIG. 3B is a schematic demonstrating signal transduction in an in vivo environment where cellular nucleic acids are present in a high background concentration, according to certain embodiments. In this environment, RNP1 302 comprising a first nucleic acid-guided nuclease 306 and a guide nucleic acid 304 (i.e., gRNA1), which comprises a region that binds to the first nucleic acid-guided nuclease 306 and is complementary to a target nucleic acid of interest 308 will combine with the target nucleic acid of interest 308. Binding of the target nucleic acid of interest 308 to RNP1 302 triggers cis and trans-cleavage activity; however, because of the high background concentration of cellular nucleic acids 320, the likelihood of trans-cleavage of the blocked second guide nucleic acid 312 is low, while the likelihood of trans-cleavage of cellular nucleic acids 320 is high, resulting in a loss of signal transduction from RNP1 302 to RNP2 (not shown). In an in vivo environment, it is not practical (or good for the cell) to provide the blocked guide nucleic acids 312 at a much higher concentration than the background cellular nucleic acids 320 and thus the trans-cleavage activity of RNP1 302, while present, is not efficiently relayed via the blocked guide nucleic acids 312 to RNP2 (not shown).

Figure 3C:
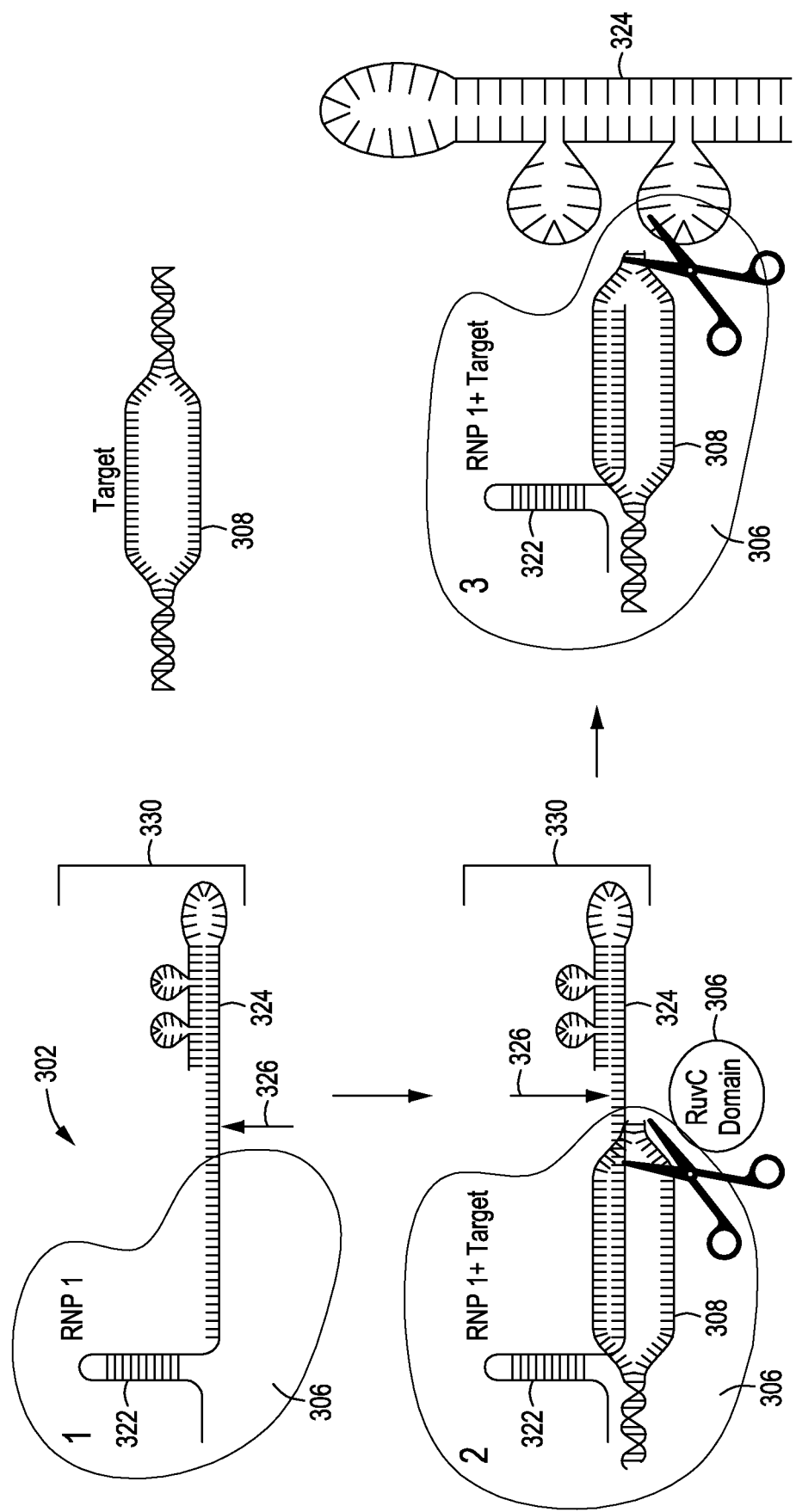
FIG. 3C is a schematic where a combination guide nucleic acid couples the first and second guide nucleic acids and thus tethers the second guide nucleic acids in proximity to RNP1 and the trans-cleavage activity generated by RNP1, according to certain embodiments.

FIG. 3C is a schematic where a combination guide nucleic acid 330, comprising both a first guide nucleic acid molecule 322 (i.e., gRNA1) specific to the target nucleic acid of interest 308 and a blocked second guide nucleic acid molecule 324 (i.e., gRNA2) specific to the effector nucleic acid (not shown), is used, according to certain embodiments. Here, gRNA1 322 and gRNA2 324 are coupled together via a nucleic acid linker 326 (here, single-stranded) which can be single- or double-stranded, DNA, RNA, a chimera of DNA and RNA, and may comprise synthetic or modified oligonucleotides to form a combination guide nucleic acid 330. Now when the presence of the target nucleic acid of interest 308 triggers cis-cleavage activity by RNP1 302, the blocked guide nucleic acid 324 is proximal to (e.g., tethered to) RNP1 302 and immediately available for trans-cleavage activity. Once the blocked guide nucleic acid 324 is unblocked, it is available for complexing with RNP2 (not shown) and for further complexing with the desired effector nucleic acid (not shown).

Figure 3D:
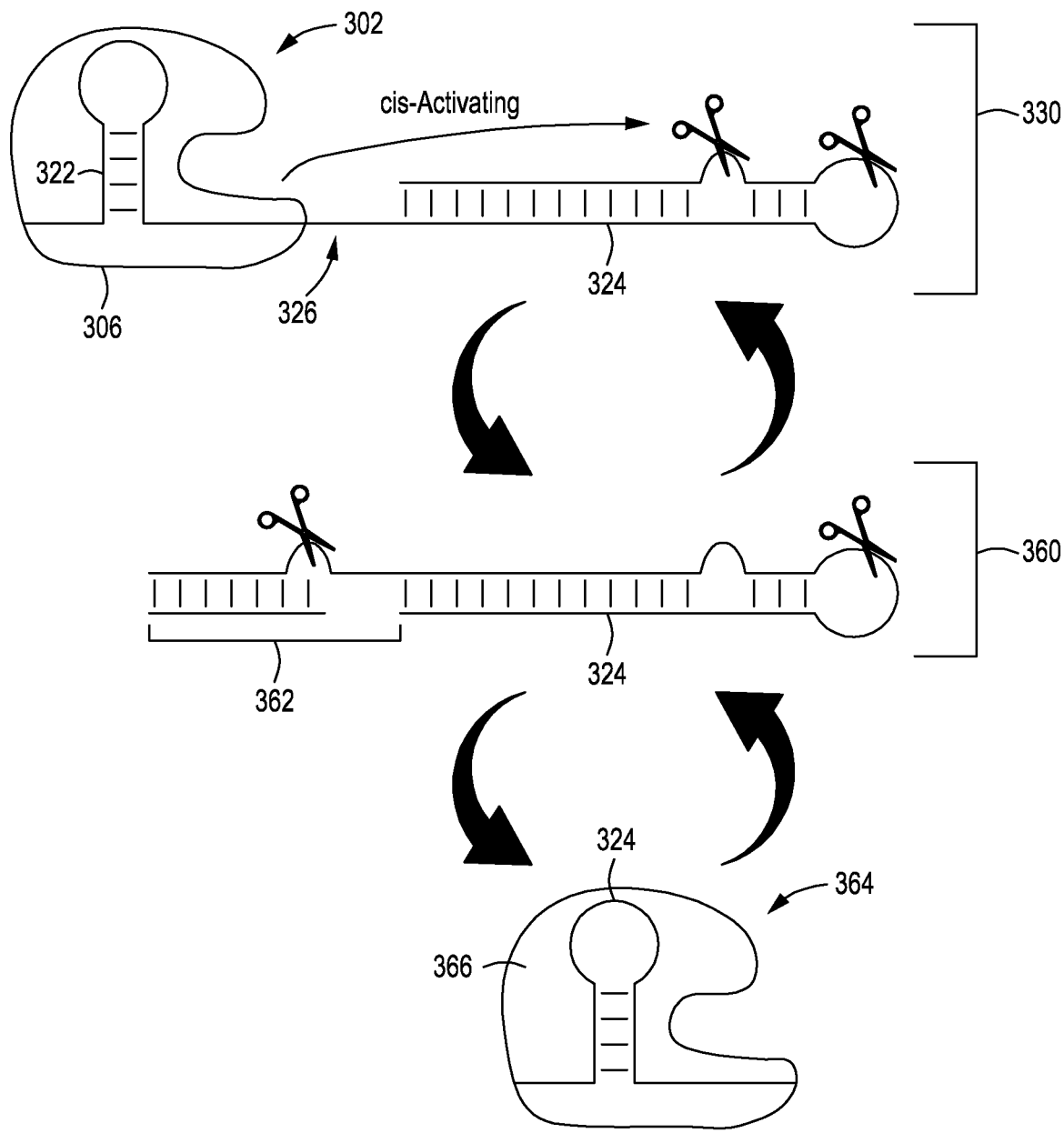
FIG. 3D is a schematic where a combination guide nucleic acid couples the first and second guide nucleic acids thus tethering the second guide in proximity to RNP1 and the trans-cleavage activity of RNP1, and further showing an amplifier molecule tethering a blocked target nucleic acid of interest to a blocked second guide nucleic acid, according to certain embodiments.

FIG. 3D is a schematic where a combination guide nucleic acid 330, comprising both a first guide nucleic acid molecule 322 (i.e., gRNA1) specific to the target nucleic acid of interest (not shown) and a blocked second guide nucleic acid molecule 324 (i.e., gRNA2) comprising a region specific to an effector nucleic acid (not shown), is present, according to certain embodiments. gRNA1 322 and gRNA2 324 are coupled together via a nucleic acid linker 326, here, single-stranded, which may comprise synthetic or modified oligonucleotides to form a combination guide nucleic acid 330. When the presence of the target nucleic acid of interest (not shown) triggers cis-cleavage activity by RNP1 302, the blocked second guide nucleic acid 324 is proximal to (e.g., tethered to) RNP1 302 and immediately available for trans-cleavage activity. Once the blocked second guide nucleic acid 324 is unblocked, it is available for complexing with a second nucleic acid-guided nuclease 366 to form RNP2 364 and complexing with the desired effector nucleic acid (not shown).

In this FIG. 3D, there is an addition of an amplifier molecule 360. Amplifier molecule 360 comprises a blocked target nucleic acid of interest 362 coupled to the blocked second guide nucleic acid molecule 324 (i.e., gRNA2) which again comprises a region specific to the effector nucleic acid. Optionally, there may be a linker present to link the blocked target nucleic acid of interest 362 to the blocked second guide nucleic acid molecule 324. The amplifier molecule 360 serves two purposes. First, the amplifier molecule 360 potentially provides more unblocked second guide nucleic acids to complex with the second nucleic acid nucleases 366 to form RNP2s 364, which in turn can complex with effector nucleic acids (not shown). Second, the amplifier molecule 360 potentially provides more unblocked target nucleic acids of interest which can complex with more RNP1s 302 and trigger more trans-cleavage activity by the RNP1s 302, thereby unblocking more blocked second guide nucleic acid molecules 324 from other amplifier molecules 360.

Figure 3E:
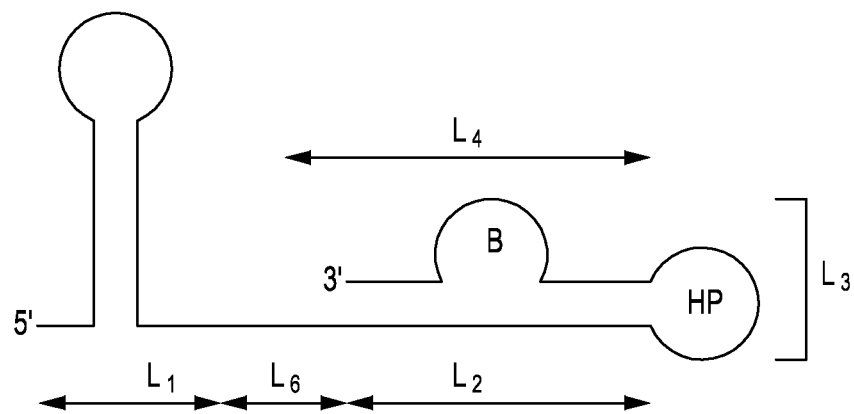
FIG. 3E is a detailed schematic of a combination guide nucleic acid, according to certain embodiments.

FIG. 3E is a detailed schematic of a combination guide nucleic acid, such as to be employed in the methods herein. L1 represents the gRNA for Cas13 (the gRNA for RNP1) comprising both the crRNA of approximately 36 nucleotides in length (e.g., for Cas13a, a 35-39 nucleotide direct repeat sequence, with a conserved 5-6 nucleotide stem and 7-9 nucleotide loop; for Cas13b, for Cas13a, a 36 nucleotide direct repeat sequence, with a conserved 3-6 nucleotide stem and 9-14 nucleotide loop; and for Cas13d, a 36 repeat sequence, with a conserved 8-10 nucleotide stem and 4-6 nucleotide loop) and a 28-30 nucleotide spacer sequence. L2 represents a 100-120 nucleotide-long segment encompassing the approximately 42 nucleotide-long gRNA for Cas12 (the gRNA for RNP2). L3 is another portion of the gRNA for Cas12 comprising a hairpin terminal loop (HP) ranging in length from 4-15 nucleotides in length. L4 is a partial complement to L2 comprising 1-3 regions of non-complementarity (i.e., loops or "bulges", "B") (here, one is shown), where the regions of non-complementarity range in size from 3-10 nucleotides. The regions of complementarity between the "bulges" are at least 5 nucleotides in length and the total length of L4 ranges from 103 to 150 nucleotides. Finally, L6 represents the single-strand linker coupling gRNA1 and blocked gRNA2 and ranges in size from 10-50 nucleotides in length.

Figure 3F:
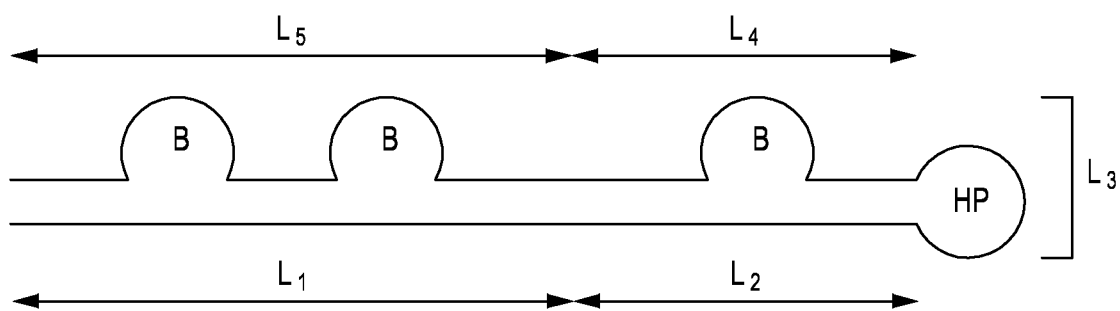
FIG. 3F is a detailed schematic of an amplifier molecule, according to certain embodiments.

FIG. 3F is a detailed schematic of an amplifier molecule, according to certain embodiments. The amplifier molecule is, again, a combination of a blocked target nucleic acid of interest (represented by L1 and L5) covalently linked to a blocked gRNA for Cas12 (the gRNA for RNP2) that will complex with the Cas12 nuclease to form RNP2; thus, L2, L3 and L4 in FIG. 3F, will be the same or similar to L2, L3 and L4 from FIG. 3E. That is, L2 ranges in length from 100-120 nucleotides and encompasses the approximately 42 nucleotide-long gRNA for Cas12, L3 comprises a hairpin terminal loop and ranges in length from 4-15 nucleotides, and L4 is a partial complement to L2 comprising 1-3 regions of non-complementarity where the regions of non-complementarity range in size from 3-10 nucleotides, the regions of complementarity between the "bulges" are at least 5 nucleotides in length, and the total length of L4 ranges from 103 to 150 nucleotides. As for the blocked target nucleic acid of interest, L1 ranges in length from 50-70 nucleotides, and L5 is a partial complement to L1 ranging in length from 53-100 nucleotides, comprising 1-3 regions of non-complementarity to L1 where the regions of non-complementarity range in size from 3-10 nucleotides and the regions of complementarity between the "bulges" range in size from 5-60 nucleotides.

Figure 4A:
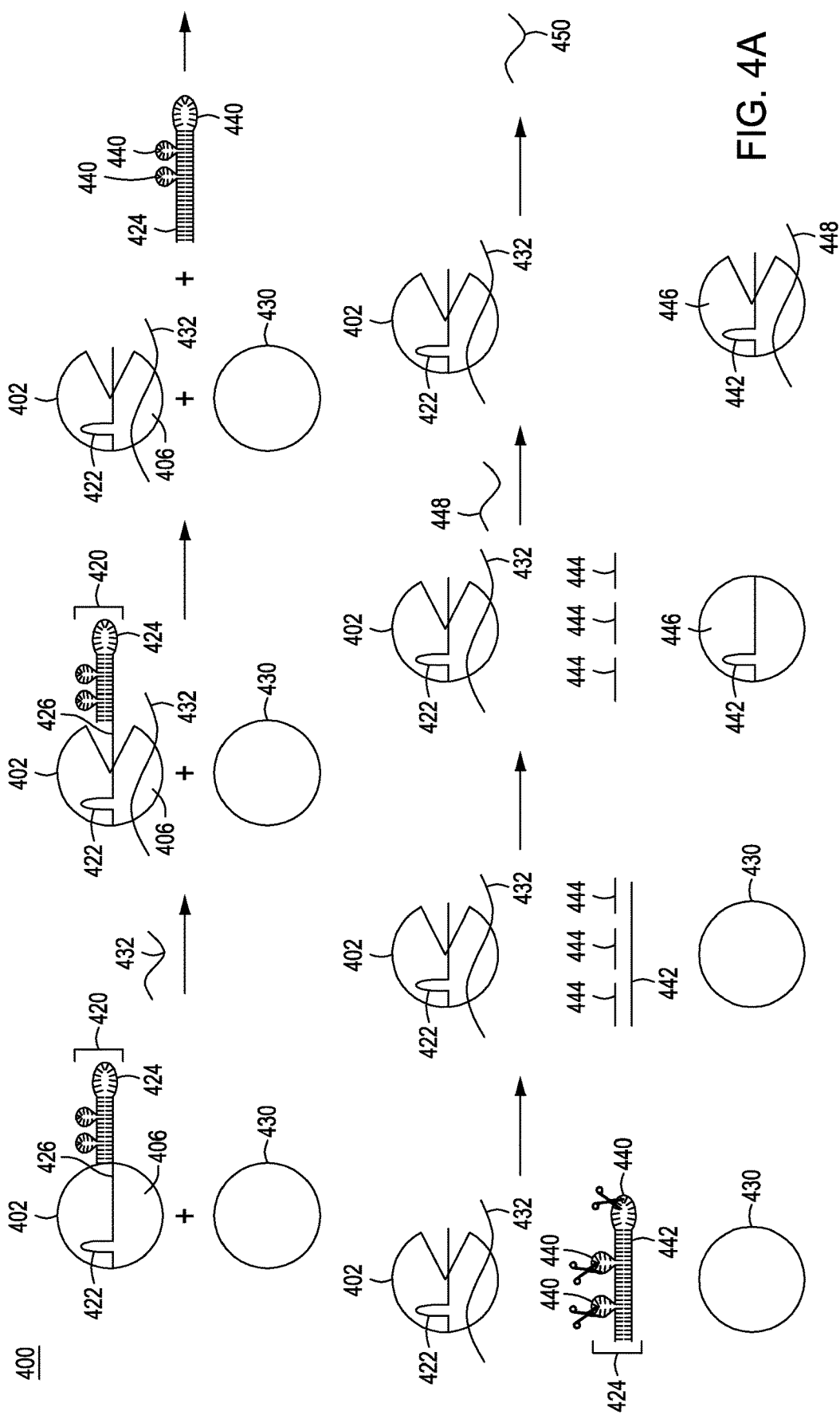
FIG. 4A is a schematic showing compositions of matter and methods to selectively activate an effector nucleic acid (i.e., effector molecule) via a CRISPR-based signal transduction cascade in vivo, according to certain embodiments.

FIG. 4A is a schematic showing compositions of matter for an exemplary method 400 used to selectively activate an effector nucleic acid via a CRISPR-based signal transduction cascade in vivo, according to certain embodiments. At top left in FIG. 4A, there is a ribonucleoprotein complex (RNP1) 402 comprising a nucleic acid-guided nuclease 406 and a combination guide nucleic acid 420. The combination guide nucleic acid comprises a first guide nucleic acid (gRNA1) 422 specific for a target nucleic acid of interest, linker 426, and blocked second guide nucleic acid (gRNA2) 424 specific for an effector. In addition to RNP1 402 in the reaction mix, there is a second nucleic acid-guided nuclease 430 (shown below combination guide nucleic acid 420). Upon detection of a target nucleic acid of interest 432—the presence of which is a proxy for an effector nucleic acid—RNP1 402 complexes with the target nucleic acid of interest 432 via first guide nucleic acid 422 and cleaves the target nucleic acid of interest 432 via cis-cleavage activity.

In addition to cis-cleavage activity, non-specific trans-cleavage activity is initiated as well thereby cleaving, inter alia, the blocked guide nucleic acid 424 from the combination guide nucleic acid. Note that in this embodiment, the linker is cleaved by trans-cleavage activity of RNP1 whereas in some embodiments the linker may not be cleavable by trans-cleavage activity. At far right at the top of FIG. 4A, the cleaved blocked guide nucleic acid 424 is seen, having two loops 440. At bottom left of FIG. 4A, the loops 440 of the blocked guide nucleic acid 424 are susceptible to cleavage by the nonspecific trans-cleavage activity of RNP1 (as was the linker in this embodiment) resulting in short oligonucleotides 444 of the complement of strand 442, where strand 442 will complex with the second nucleic acid-guided nuclease 430 to form RNP2. Although the linker 426 is shown here as being cleaved first followed by cleavage of the loops 440 in the blocked guide nucleic acid 424, in reality the cleavage of the linker 426 and the loops 440 would likely be simultaneous or nearly so. Cleavage of loops 440 and de-hybridization of short oligonucleotides 444 result in an unblocked guide nucleic acid 442 that can combine with second nucleic acid-guided nuclease 430 to form a second ribonucleoprotein complex 446 (i.e., RNP2). Once RNP2 446 is formed, an effector nucleic acid 448 can complex with RNP2 446, thereby activating RNP2 446, and where the effector 448 is altered resulting in effector 450, which then can complex with or alter an effector target (not shown).

Figure 4B:
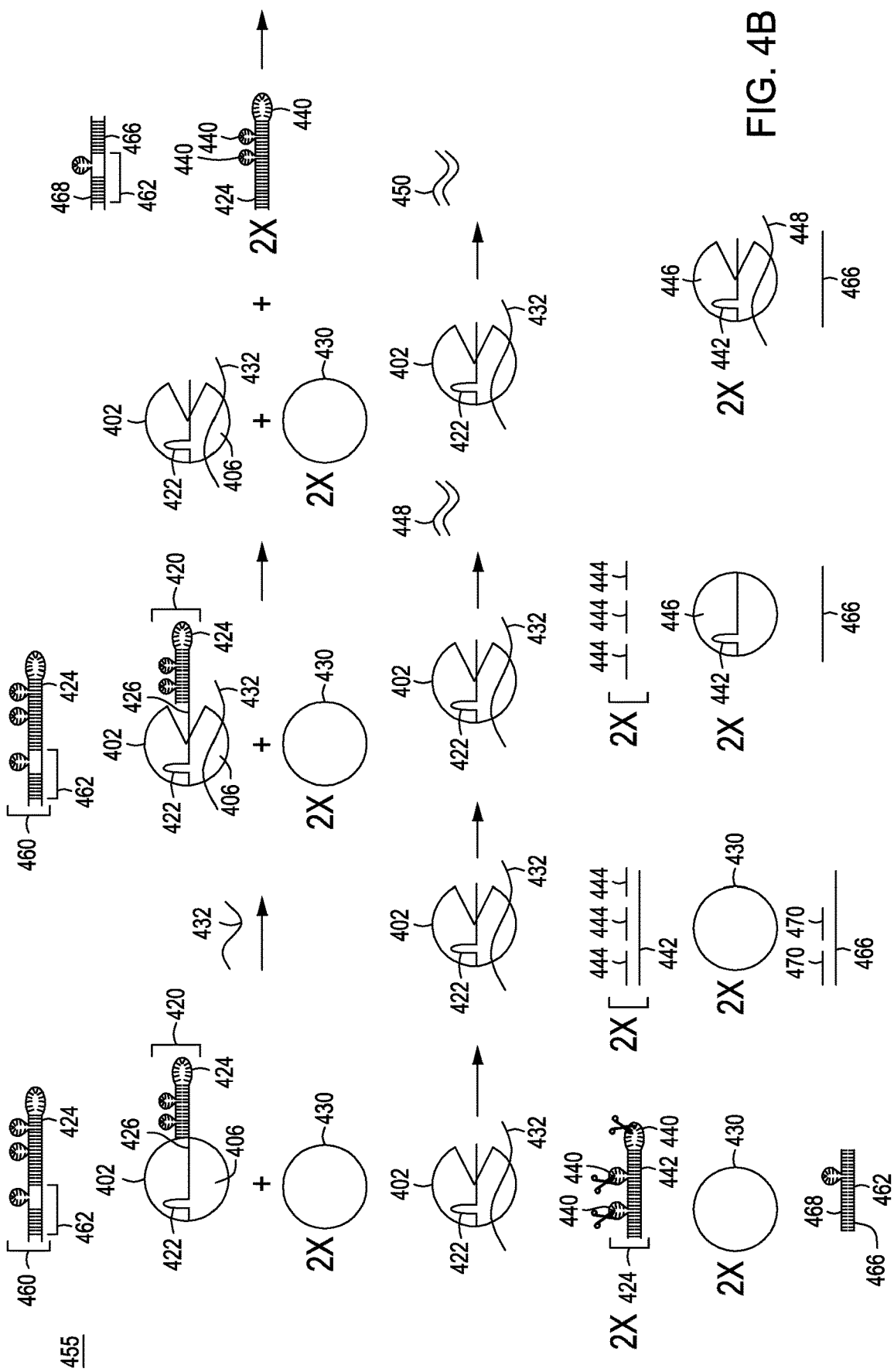
FIG. 4B is a schematic showing compositions of matter and methods to selectively activate an effector nucleic acid via a CRISPR-based signal transduction cascade employing an amplifier molecule, according to certain embodiments.

FIG. 4B is a schematic showing compositions of matter for an alternative exemplary method 455 used to selectively activate an effector nucleic acid via a CRISPR-based signal transduction cascade in vivo, according to certain embodiments. At top left in FIG. 4B, there is a ribonucleoprotein complex (RNP1) 402 comprising a nucleic acid-guided nuclease 406 and a combination guide nucleic acid 420. The combination guide nucleic acid comprises a first guide nucleic acid (gRNA1) 422 specific for a target nucleic acid of interest, linker 426, and blocked second guide nucleic acid (gRNA2) 424 specific for an effector. In addition to RNP1 402 in the reaction mix, there are two second nucleic acid-guided nucleases 430 and an amplifier molecule 460 comprising a blocked target nucleic acid of interest 462 coupled to another blocked guide nucleic acid 424. Upon detection of a target nucleic acid of interest 432—the presence of which is a proxy for an effector nucleic acid—RNP1 402 complexes with the target nucleic acid of interest 432 via the first guide nucleic acid 422 and cleaves the target nucleic acid of interest 432 via cis-cleavage activity. In addition to the cis-cleavage activity, non-specific trans-cleavage activity is initiated thereby cleaving, inter alia, the blocked second guide nucleic acid 424 from the combination guide nucleic acid and further cleaving the blocked target nucleic acid of interest 462 from the other blocked second guide nucleic acid 424 in amplifier molecule 460.

Again, note that in this embodiment the linkers 426 of the combination guide nucleic acid is cleaved by trans-cleavage activity of RNP1 whereas in some embodiments the linker may not be cleavable by trans-cleavage activity. At far right at the top of FIG. 4B, 2× cleaved blocked guide nucleic acids 424 are seen having two loops 440, and blocked target nucleic acid of interest 462 is also seen. Blocked target nucleic acid of interest 462 comprises target strand 466 and non-target strand 468. At bottom left of FIG. 4B, the loops 440 of the two blocked guide nucleic acids 424 are susceptible to cleavage by the nonspecific trans-cleavage activity of RNP1 resulting in short oligonucleotides 444 of the complement of strand 442, and it is strand 442 that will complex with the second nucleic acid-guided nuclease to form RNP2. Again, although the linker 426 is shown here as being cleaved first followed by cleavage of the loops 440 in the blocked guide nucleic acid 424, in reality the cleavage of the linker 426 and the loops 440 would likely be simultaneous or nearly so. Cleavage of loops 440 and de-hybridization of short oligonucleotides 444 result in two unblocked guide nucleic acids 442 that can combine with two second nucleic acid-guided nucleases 430 to form two second ribonucleoprotein complexes 446 (i.e., RNP2s). Once the two RNP2s 446 are formed, effector nucleic acids 448 can complex with the RNP2s 446, activating the RNP2s 446 and thereby altering the effectors 448 resulting in effectors 450, which then can complex with or alter an effector target (not shown).

In addition, note following from left to right at bottom of FIG. 4B, the loop in the blocked target nucleic acid of interest portion 462 of the amplifier molecule 460 also is cleaved by the trans-cleavage activity of RNP1 402, thereby unblocking the blocked target nucleic acid of interest 462 and resulting in target strand 466 and non-target strand fragments 470. Target strand 466 of the unblocked target nucleic acid of interest is not free to complex with additional RNP1s (additional RNP1s not shown).

Target Nucleic Acids of Interest, Effector Nucleic Acids and Effector Targets

The target nucleic acid of interest may be any nucleic acid molecule in a cell that is used to identify cells comprising an effector nucleic acid that one desires to alter. The target nucleic acid may be a gene sequence, a control sequence (i.e., promoter, enhancer, terminator), an mRNA transcript, etc. The effector nucleic acids are any nucleic acids in the cell that are to be changed (e.g., edited, knocked-out, or modified so as to up-regulate or down-regulate an effector target) by the action of RNP2, where the effector nucleic acids include DNA coding, control, repetitive and intronic sequences, mRNA transcripts and rRNA sequences.

As used herein, the effector is a nucleic acid molecule upon which a ribonucleoprotein complex (here, RNP2) acts to regulate biological activity of a cell. RNP2 comprises 1) a formerly blocked second guide nucleic acid molecule that has been unblocked; and 2) a nucleic acid-guided nuclease. The unblocked guide nucleic acid has sequence specificity for the effector nucleic acid. RNP2 may alter the effector nucleic acid in any number of ways, including making single nucleotide substitutions, multiple nucleotide substitutions, insertions, deletions, and the like. The "target strand" of an effector nucleic acid (whether single- or double-stranded) is the strand of the effector nucleic acid that is complementary to the unblocked guide nucleic acid. The spacer sequence of the unblocked guide nucleic acid may have 50%, 60%, 75%, 80%, 85%, 90%, 95%, 97.5%, 98%, 99% or more complementarity to the effector nucleic acid. Optimal alignment can be determined with the use of any suitable algorithm for aligning sequences. Full complementarity is not necessarily required provided there is sufficient complementarity to cause hybridization between the RNP2 complex and the effector nucleic acid.

An effector nucleic acid ("effector") can include any polynucleotide, such as DNA (ssDNA or dsDNA) or RNA polynucleotides, and may be located in the nucleus or cytoplasm of a cell such as, for example, within an organelle of a eukaryotic cell, such as a mitochondrion or a chloroplast, or it can be exogenous to a host cell. The effector nucleic acid may be associated with a protospacer adjacent motif (PAM) sequence, which may include a 2-5 base pair sequence adjacent to the protospacer. In some embodiments, 1, 2, 3, 4, 5, 6, 7, 8, 9, 10 or more effector nucleic acids can be impacted by the disclosed method. Effectors can be activators that promote transcription and/or translation of a nucleic acid sequence, repressors that prevent transcription and/or translation of a nucleic acid sequence, the effector itself may be therapeutic or the effector itself may be transcribed.

As used herein, an "effector target" is a molecule in a cell on which an effector nucleic acid acts. An effector target may be a nucleic acid (coding, non-coding or regulatory sequence in genomic or episomal DNA, or the effector nucleic acid itself), a peptide, a lipid, a sugar, a glycoprotein, a small molecule, or the effector target may be a chimera or any portion of any of these molecules.

Nucleic Acid-Guided Nucleases

The cascade systems comprise delivery of nucleic acid-guided nucleases to a cell in vivo, either provided as a protein, a coding sequence for the protein, or as a ribonucleoprotein complex. In some embodiments, the one or more nucleic acid-guided nucleases in the reaction mix may be, for example, a Cas nucleic acid-guided nuclease. Any nucleic acid-guided nuclease having both cis- and trans-cleavage activity may be employed for RNP1, and the same nucleic acid-guided nuclease may be used for both RNP complexes or different nucleic acid-guided nucleases may be used in RNP1 and RNP2. The nucleic acid-guided nuclease in RNP2 need not necessarily have trans-cleavage activity. Trans-cleavage activity of the first nucleic acid nuclease (or the second nucleic acid nuclease) is not triggered unless and until a target nucleic acid of interest binds RNP1 or an effector nucleic acid binds RNP2.

Nucleic acid-guided nucleases for use in the methods and compositions described herein include Type V and Type VI nucleic acid-guided nucleases, as well as nucleic acid-guided nucleases that comprise a RuvC nuclease domain or a RuvC-like nuclease domain but lack an HNH nuclease domain. Nucleic acid-guided nucleases with these properties are reviewed in Makarova and Koonin, Methods Mol. Biol., 1311:47-75 (2015) and Koonin, et al., Current Opinion in Microbiology, 37:67-78 (2020) and updated databases of nucleic acid-guided nucleases and nuclease systems that include newly-discovered systems include BioGRID ORCS (orcs:thebiogrid.org); GenomeCRISPR (genomecrispr.org); Plant Genome Editing Database (plantcrispr.org) and CRIS-PRCasFinder (crispercas.i2bc.paris-saclay.fr).

The type of nucleic acid-guided nuclease utilized in the method of detection depends on the type of target nucleic acid of interest to be detected. For example, a DNA nucleic acid-guided nuclease (e.g., a Cas12a, Cas14a, or Cas3) should be utilized if the target nucleic acid of interest (RNP1) or effector nucleic acid (RNP2) is a DNA molecule, and an RNA nucleic acid-guided nuclease (e.g., Cas13a or Cas12g) should be utilized if the target nucleic acid of interest (RNP1) or effector nucleic acid (RNP2) is an RNA molecule. Exemplary nucleic acid-guided nucleases include, but are not limited to, Cas RNA-guided DNA nucleic acid-guided nucleases, such as Cas3, Cas12a (e.g., AsCas12a, LbCas12a), Cas12b, Cas12c, Cas12d, Cas12e, Cas14, Cas12h, Cas12i, and Cas12j; Cas RNA-guided RNA nucleic acid-guided nucleases, such as Cas13a (LbaCas13, LbuCas13, LwaCas13), Cas13b (e.g., CccaCas13b, PsmCas13b), and Cas12g; and any other nucleic acid (DNA, RNA, or cDNA) targeting nucleic acid-guided nuclease with cis-cleavage activity and collateral trans-cleavage activity. In some embodiments, the nucleic acid-guided nuclease is a Type V CRISPR-Cas nuclease, such as Cas12a, Cas13a, or Cas14a. In some embodiments, the nucleic acid-guided nuclease is a Type I CRISPR-Cas nuclease, such as Cas3. Type II and Type VI nucleic acid-guided nucleases may also be employed.

The nucleic acid nucleases may be, e.g., Cas 13a or Cas12g in RNP1 and in RNP2 for, e.g., an RNA trigger for an RNA knockdown; Cas 13a or Cas12g in RNP1 and Cas12a in RNP2 for, e.g., an RNA trigger for a DNA edit; for Cas 12a in RNP1 and Cas12a in RNP2 for, e.g., a DNA trigger for a DNA edit.

Guide RNA (gRNA)

The present disclosure triggers an effector nucleic acid upon detection of a target nucleic acid of interest using first and second guide nucleic acids (gRNAs) linked to one another. The first guide nucleic acid (i.e., gRNA1) comprises a sequence specific to a target nucleic acid of interest and is coupled to the blocked second guide nucleic acid (i.e., gRNA2) via a linker. The blocked second guide nucleic acid is blocked when initially linked to the first guide nucleic acid but becomes unblocked upon initiation of trans-cleavage activity by RNP1. The second guide nucleic acid has a sequence specific to an effector nucleic acid.

Like the nucleic acid-guided nuclease, the combination guide nucleic acid may be provided in the cascade reaction mix in a preassembled RNP, as an RNA molecule, or may also be provided as a DNA sequence to be transcribed, in, e.g., a vector backbone.

A blocked guide nucleic acid may be single-stranded or double-stranded, circular or linear, and may further contain a partially hybridized nucleic acid sequence containing cleavable secondary loop structures. Such blocked guide nucleic acids typically have a low binding affinity, or high dissociation constant ($K_d$) in relation to binding to an effector nucleic acid and may be referred to herein as a high $K_d$ nucleic acid molecule. In the context of the present disclosure, the binding of blocked or unblocked guide molecules to RNP2, low $K_d$ values range from about 100 fM to about 1 aM or lower (e.g., 100 zM) and high $K_d$ values are in the range of 100 nM to about 10-100 10 mM and thus are about $10^5$-, $10^6$-, $10^7$-, $10^8$-, $10^9$- to $10^{10}$-fold or higher as compared to low $K_d$ values. Of course, the ideal blocked guide nucleic acid would have an "infinite $K_d$."

Thus, the blocked guide nucleic acids (high $K_d$ molecules) described herein can be converted into unblocked guide nucleic acids (low $K_d$ molecules—also in relation to binding to an effector nucleic acid) via cleavage of nuclease-cleavable regions (e.g., via active RNP1s and RNP2s). The unblocked guide nucleic acid has a higher binding affinity for the effector molecule or nucleic acid than does the blocked guide nucleic acid.

In embodiments where blocked guide nucleic acids are linear and/or form a secondary structure, the blocked guide nucleic acids may be single-stranded (ss) or double-stranded (ds) and contain a first nucleotide sequence and a second nucleotide sequence. The first and second nucleotide sequences of a blocked guide nucleic acid may be on the same nucleic acid molecule (e.g., for single-strand embodiments) or on separate nucleic acid molecules (e.g., for double-strand embodiments). Trans-cleavage (e.g., via RNP1 or RNP2) of the second nucleotide sequence in the blocked guide nucleic acid converts the blocked guide nucleic acid to a single-strand unblocked guide nucleic acid. The unblocked guide nucleic acid contains only the first nucleotide sequence, which has sufficient complementarity to hybridize to the effector molecule.

In some embodiments, the second nucleotide sequence at least partially hybridizes to the first nucleotide sequence, resulting in a secondary structure containing at least one loop (e.g., hairpin loops, tetraloops, pseudoknots, junctions, kissing hairpins, internal loops, bulges, and multibranch loops). Such loops block the blocked guide nucleic acids from binding or incorporating into an RNP complex thereby initiating cis- or trans-cleavage.

In some embodiments, the blocked guide nucleic acids (i.e., high $K_d$ guide nucleic acids in relation to binding to the effector molecule) of the disclosure may include a structure represented by Formula I, Formula II, Formula III, or Formula IV wherein Formulas I-IV are in the 5'-to-3' direction:

A-(B-L)J-C-M-T-D (Formula I);

wherein A is 0-15 nucleotides in length;
B is 4-12 nucleotides in length;
L is 3-25 nucleotides in length;
J is an integer between 1 and 10;
C is 4-15 nucleotides in length;
M is 1-25 nucleotides in length or is absent, wherein if M is absent then A-(B-L)J-C and T-D are separate nucleic acid strands;
T is 17-135 nucleotides in length (e.g., 17-100, 17-50, or 17-25) and comprises a sequence complementary to B and C; and
D is 0-10 nucleotides in length and comprises a sequence complementary to A;

D-T-T'-C-(L-B)J-A (Formula II);

wherein D is 0-10 nucleotides in length;
T-T' is 17-135 nucleotides in length (e.g., 17-100, 17-50, or 17-25);
T' is 1-10 nucleotides in length and does not hybridize with T;
C is 4-15 nucleotides in length and comprises a sequence complementary to T;
L is 3-25 nucleotides in length and does not hybridize with T;
B is 4-12 nucleotides in length and comprises a sequence complementary to T;
J is an integer between 1 and 10;
A is 0-15 nucleotides in length and comprises a sequence complementary to D;

T-D-M-A-(B-L)J-C (Formula III);

wherein T is 17-135 nucleotides in length (e.g., 17-100, 17-50, or 17-25);
D is 0-10 nucleotides in length;
M is 1-25 nucleotides in length or is absent, wherein if M is absent then T-D and A-(B-L)J-C are separate nucleic acid strands;
A is 0-15 nucleotides in length and comprises a sequence complementary to D;
B is 4-12 nucleotides in length and comprises a sequence complementary to T;
L is 3-25 nucleotides in length;
J is an integer between 1 and 10; and
C is 4-15 nucleotides in length;

T-D-M-A-Lp-C (Formula IV);

wherein T is 17-31 nucleotides in length (e.g., 17-100, 17-50, or 17-25);
D is 0-15 nucleotides in length;
M is 1-25 nucleotides in length;
A is 0-15 nucleotides in length and comprises a sequence complementary to D; and
L is 3-25 nucleotides in length;
p is 0 or 1;
C is 4-15 nucleotides in length and comprises a sequence complementary to T.

In alternative embodiments of any of these molecules, T (or T-T') can have a maximum length of 1000 nucleotides, e.g., at most 750, at most 500, at most 400, at more 300, at most 250, at most 200, at most 150, at most 135, at most 100, at most 75, at most 50, or at most 25 nucleotides. For more information about Formulas I-IV, see U.S. Ser. Nos. 17/861,207; 17/861,208; and 17/861,209, filed 9 Jul. 2022.

Nucleotide mismatches can be introduced in any of the above structures containing double-strand segments (for example, where M is absent in Formula I or Formula III) to reduce the melting temperature ($T_m$) of the segment such that once the loop (L) is cleaved, the double-strand segment is unstable and dehybridizes rapidly. The percentage of nucleotide mismatches of a given segment may vary between 0% and 50%; however, the maximum number of nucleotide mismatches is limited to a number where the secondary loop structure still forms. "Segments" in the above statement refers to A, B, and C. In other words, the number of hybridized bases can be less than or equal to the length of each double-strand segment and vary based on number of mismatches introduced.

In any of the foregoing embodiments, the blocked guide nucleic acid may be a modified or non-naturally occurring nucleic acid molecule. In some embodiments, the blocked guide nucleic acids of the disclosure may further contain a locked nucleic acid (LNA), a bridged nucleic acid (BNA), and/or a peptide nucleic acid (PNA). The blocked guide nucleic acid may contain a modified or non-naturally occurring nucleoside, nucleotide, and/or internucleoside linkage, such as a 2'-O-methyl (2'-O-Me) modified nucleoside, a 2'-fluoro (2'-F) modified nucleoside, and a phosphorothioate (PS) bond, any other nucleic acid molecule modifications described above, and any combination thereof.

In some embodiments, the blocked guide nucleic acids provided herein are circular DNAs, RNAs or chimeric (DNA-RNA) molecules, and the blocked nucleic acid molecules may include different base compositions depending on the Cas enzyme used for RNP1 and RNP2. For the circular design of blocked nucleic acid molecules, the 5' and 3' ends are covalently linked together. This configuration makes internalization of the blocked guide nucleic acid into RNP2—and subsequent RNP2 activation—sterically unfavorable, thereby blocking the progression of the cascade system. Thus, RNP2 activation (e.g., trans-cleavage activity) happens after cleavage of a portion of the blocked guide nucleic acid followed by linearization and internalization of unblocked guide nucleic acid into RNP2.

In some embodiments, the blocked guide nucleic acid molecules are topologically circular molecules with 5' and 3' portions hybridized to each other using DNA, RNA, LNA, BNA, or PNA bases which have a very high melting temperature ($T_m$). The high $T_m$ causes the structure to effectively behave as a circular molecule even though the 5' and 3' ends are not covalently linked. The 5' and 3' ends can also have base non-naturally occurring modifications such as phosphorothioate bonds to provide increased stability.

In embodiments where the blocked guide nucleic acids are circularized (i.e., circular or topologically circular), each blocked nucleic acid molecule includes a first region, which is a target sequence specific to the gRNA of RNP2, and a second region, which is a sequence that can be cleaved by nuclease enzymes of activated RNP1 and/or RNP2. The first region may include a nuclease-resistant nucleic acid sequence such as, for example, a phosphorothioate group or other non-naturally occurring nuclease-resistant base modifications, for protection from trans-nucleic acid-guided nuclease activity.

Linkers

For the linkers used to couple the two guide nucleic acid molecules in the combination guide nucleic acid, the residues of the linker may be wholly or partially modified. Modifications typically are achieved by the incorporation of, for example, one or more alternative nucleosides, alternative sugar moieties, and/or alternative internucleoside linkages. The linkers may comprise RNA, DNA, LNAs, PNAs, as well as internucleoside modifications such as phosphorothioates, phosphorodithioates, phosphotriesters, aminoalkylphosphotriesters, methyl and other alkyl phosphonates including 3'-alkylene phosphonates, 5'-alkylene phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, and boranophosphates having normal 3'-5' linkages, 2'-5' linked analogs of these, and those having inverted polarity wherein one or more internucleotide linkages is a 3' to 3', 5' to 5' or 2' to 2' linkage. The linkers may or not be cleaved from the trans-cleavage activity of RNP1 or RNP2 when the blocked guided nucleic acids are unblocked. The linkers may be single-stranded or double-stranded, cleavage or non-cleavable, and may be DNA, RNA or a mix of DNA and RNA.

Testing the In Vivo Cascade System

FIGS. 5A-5D show four schematics of in vitro experimental schemes for assessing components of the present systems for activating effector molecules in vivo and Examples I-VI describe experimental schemes performed for assessing components of the present systems for activating effector molecules in vivo.

Figure 5A:
FIG. 5A is a schematic showing a first experimental scheme to assess cellular RNP1→RNP2 signal transfer in the cascade system, according to certain embodiments.

FIG. 5A is a schematic showing a first experimental scheme to assess cellular RNP1-RNP2 signal transfer, according to certain embodiments. At step 1, a commercially available HEK293 cell line expressing green fluorescent protein (GFP) under the control of the CMV promoter is transduced with combinations of RNP1 (comprising the first nucleic acid-guided nuclease and the first guide nucleic acid), an exogenous RNA target for RNP1, the blocked second guide nucleic acid and the second nucleic acid-guided nuclease. In this example, the cascade system components are delivered to the cells as sequences to be transcribed (e.g., gRNA sequences) and coding sequences (e.g., for the nucleic acid-guided nucleases) on lentiviral vectors. The blocked second guide nucleic acid is complementary to the effector nucleic acid—here, a nucleic acid that when altered knocks out transcription of GFP—in the cell.

Step 2 shows that the presence of the target nucleic acid of interest (i.e., the exogenous RNA target for RNP1) allows for formation of the target/RNP1 complex and triggering of cis- and trans-cleavage by RNP1. In the presence of trans-cleavage, the blocked guide nucleic acid becomes unblocked and combines with the second nucleic acid-guided nuclease to form RNP2. RNP2 is now available to complex with and act upon an effector nucleic acid in the cell, which in this case is a GFP knockout. The successful readout results in GFP knockout (no GFP expression) in the presence of the RNA target for RNP1, and no GFP knockout (GFP expression) in the absence of the RNA target for RNP.

To perform this first experimental scheme, GFP.293T cells are obtained from a commercial vendor and the sequence of the GFP transgene sequence is confirmed to ensure RNP2 guide fidelity. The blocked guide nucleic acid corresponding to the GFP transgene is then designed and synthesized. Commercially available RNA (mCherry) with a known sequence and guide nucleic acid against it are obtained. The exogenous RNA is transfected into the GFP.293T cells with and without the first nucleic acid-guided nuclease to confirm exogenous translation (mCherry+) and to confirm RNA1-dependent knockdown, efficacy and kinetics.

Figure 5B:
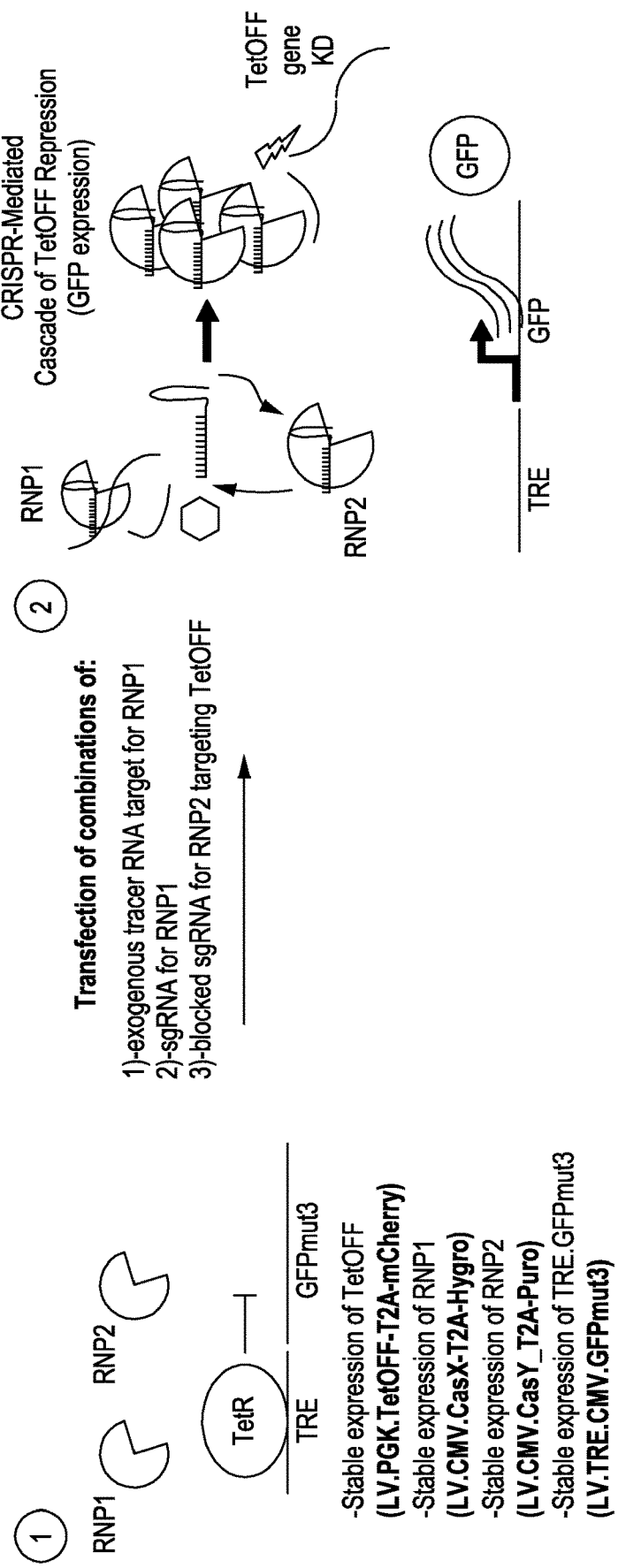
FIG. 5B is a schematic showing a second experimental scheme to assess kinetics and specificity of the signal transduction cascade system in cells in vivo using a Tet-repression system, according to certain embodiments.

FIG. 5B is a schematic showing a second experimental scheme to assess kinetics and specificity of the signal transduction cascade system in cells in vivo using a Tet-repression system, according to certain embodiments. At left of FIG. 5B, cells are transduced to stably express TetOFF (which is the Tet repressor), the first nucleic acid-guided nuclease for RNP1, the second nucleic acid-guided nuclease, and GFPmut3 where GFPmut 3 is under the control of the Tet-repressed promoter. Into this cell line is transfected an exogenous RNA for RNP1, a first guide nucleic acid for RNP1 and a blocked second guide nucleic acid targeting TetOFF.

At step 2, the presence of the target nucleic acid of interest (i.e., the exogenous RNA target for RNP1) allows for formation of the target/RNP1 complex and triggering of cis- and trans-cleavage by RNP1. In the presence of trans-cleavage, the blocked guide nucleic acid becomes unblocked and combines with the second nucleic acid-guided nuclease to form RNP2. RNP2 is now available to complex with and act upon an effector nucleic acid in the cell, which in this case is TetOFF. With the Tet repressor knocked out, expression of GFPmut3 can take place resulting in fluorescence. A successful readout results in GFP knockout in the presence of the RNA target for RNP1, and no GFP knockout in the absence of the RNA target for RNP1.

To test the reporter system for the second experimental scheme, the LV.TRE.CMV.GFPmut3 and LV.TetOFF-2A-mCherry lentiviral constructs are designed and synthesized. 293T/3T3 cells are transduced with LV.TRE.CMV.GFPmut3, and GFP+ cells are selected. The GFP+ cells are then transduced with the LV.TetOFF-2A-mCherry lentiviral constructs, and GFP− and mCherry+ clones are selected. GFP expression is then confirmed after 48-72 hours of DOX treatment. To develop the in vivo cascade system, LV.CMV.CasX-T2A-Hygro and LV.CMV.CasY-T2A-Puro constructs are designed and synthesized, which provide the coding sequences for the first and second nucleic acid-guided nucleases. The cells are then transduced with the lentiviral constructs and clones are selected following Hygro/Puro selection. Exogenous RNA (i.e., the target nucleic acid of interest), the first guide nucleic acid, and the blocked second guide nucleic acid in various combinations are provided to the cells, where confirmation of guide design and signal transfer is performed as described above for the first experimental scheme.

Figure 5C:
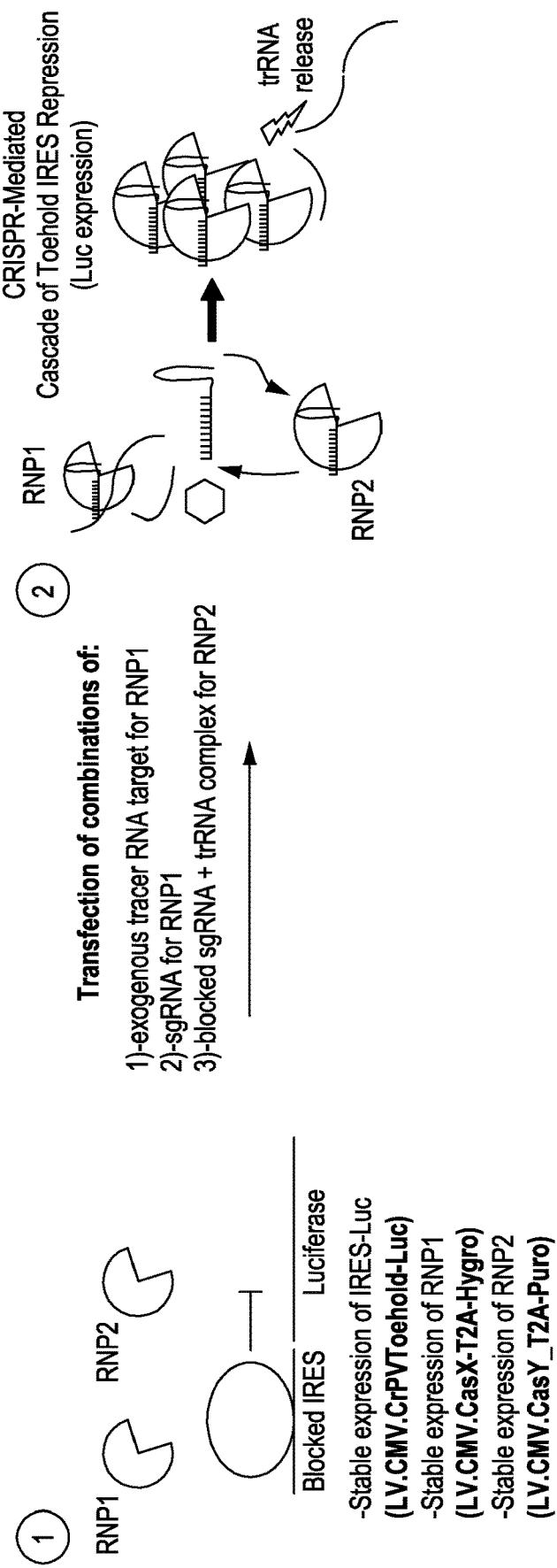
FIG. 5C is a schematic showing a third experimental scheme to assess kinetics and specificity of the signal transduction cascade system in cells in vivo using an RNA-responsive system, according to certain embodiments.

FIG. 5C is a schematic showing a third experimental scheme to assess kinetics and specificity of the signal transduction cascade system in cells in vivo using an RNA-responsive system, according to certain embodiments. The aim of this third experimental scheme is to assess whether a single transcript delivery system works for the in vivo cascade system. At step 2 at left in FIG. 5C shows RNP1 and RNP2 and a blocked internal ribosome entry site (IRES) preventing transcription of the luciferase gene. A cell line is transduced to stably express IRES-Luc, the first nucleic acid-guided nuclease, and the second nucleic acid-guided nuclease. Into this cell line is transfected an exogenous RNA for RNP1, a guide nucleic acid for RNP1, and a blocked second guide nucleic acid for RNP2.

At step 2, the presence of the target nucleic acid of interest (i.e., the exogenous RNA target for RNP1) allows for formation of the target/RNP1 complex and triggering of cis- and trans-cleavage by RNP1. In the presence of trans-cleavage, the blocked guide nucleic acid becomes unblocked and combines with the second nucleic acid-guided nuclease to form RNP2. RNP2 is now available to complex with and act upon an effector nucleic acid in the cell, which in this case comprises trigger RNAs that unblock the IRES resulting in luciferase expression. A successful readout results in luciferase expression in the presence of the RNA target for RNP1, and no luciferase expression in the absence of the RNA target for RNP1.

Figure 5D:
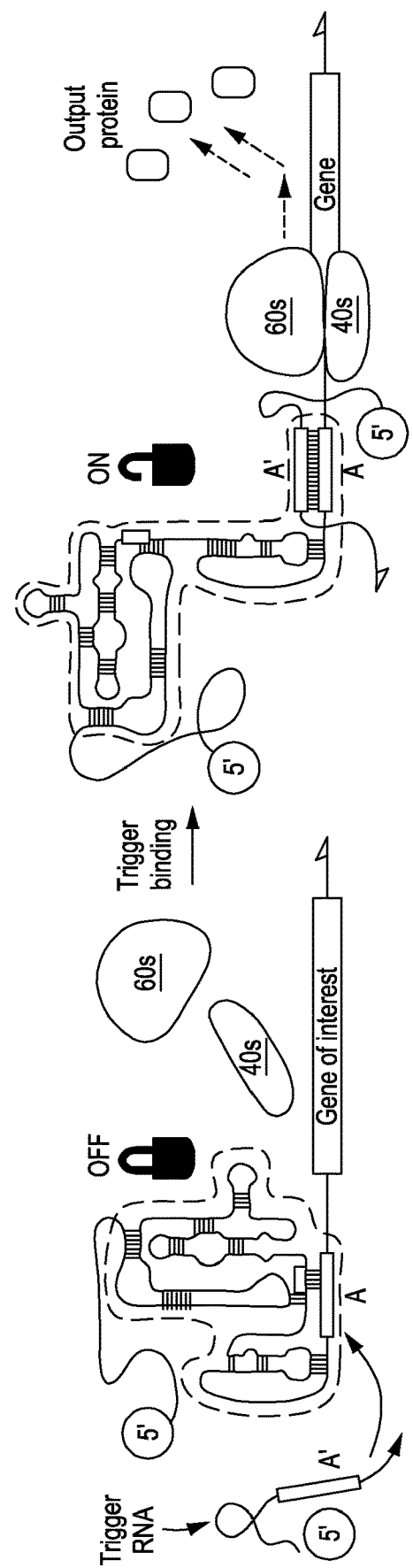
FIG. 5D shows the mechanism of action of the third experimental scheme, according to certain embodiments.

FIG. 5D shows the mechanism of action of the third experimental scheme. For more information regarding this experimental scheme, see Zhao, et al., Nat. Biotech., 40:539-45 (2022).

In Vivo Delivery of Therapeutic Components

Lipid nanoparticles (LNPs) present a novel nanoparticle drug delivery system that can be used to deliver a wide range of therapeutic agents, including poorly soluble drugs, proteins and peptides (such as the ribonucleoprotein complexes and nucleic acid-guided nucleases of the CRISPR-based therapeutic system described herein) and nucleic acids such as DNA and RNA (including the amplifier molecules of the CRISPR-based therapeutic system). LNPs are made of ionizable lipids, which are positively charged at low pH but neutral at physiological pH. LNPs typically have a spherical shape with an average diameter between 10 and 1000 nanometers. These unique properties allow the LNPs and their payloads to be taken into cells via receptor-mediated endocytosis. LNPs can be targeted to specific cells or tissues, making them ideal for cancer therapies and other diseases; they are biocompatible and biodegradable, thus avoiding the risk of side effects and adverse events; and finally they are non-immunogenic, meaning that they do not illicit an immune response. Overall, LNPs present a low toxicity profile. See generally, Montolo, et al., Front. Mol. Biosci., vol. 7, 30 Oct. 2020; and Duan, et al., RSC Adv. 10:26777-791 (2020).

LPNs can be formulated via several different methods and new protocols are being developed as the field progresses. High-pressure homogenization has been used widely, providing an effective and reliable means to prepare LPNs on a large scale. High-pressure homogenization can be hot or cold. With hot high-pressure homogenization, the lipid is melted, then the therapeutic agent is dissolved into it. A hot aqueous surfactant solution is added and dispersed with a high shear mixing device. The pre-emulsion is homogenized to reach the desired particle size, then the nano-emulsion is cooled. While cooling, the liquid droplets crystallize and form solid matrix LNPs.

Cold high-pressure homogenization uses a similar process; however, after combining the lipid and therapeutic agent, the mixture is cooled with liquid nitrogen or dry ice and milled into microparticles, which are then homogenized into nanoparticles.

LNPs also can be prepared by emulsion-sonication. In this process, the lipid is, the therapeutic agent is dissolved into it, and a hot aqueous surfactant solution is added and dispersed with a high shear mixing device. Following dispersion, a probe solicitor is used to ultrasonicate the emulsion to form nanoparticles, which form as the emulsion is cooled. Other methods include the solvent emulsification-diffusion method, solvent emulsification-evaporation method, double emulsification method, phase inversion temperature method, membrane contractor method, supercritical fluid-based methods, and others (for details describing these methods and others, see, e.g., Duong, et al., Molecules, 25(20):4781 (2020); and Sastri, et al., J. App. Pharm. Sci., 10(06):126-141 (2020)).

In addition to LNPs, viral vectors may be used to introduce the cascade assay components into a subject. Because the payload for the assay components may be large—e.g., approximately 15 kb for each enzyme if there are two different enzymes in each of RNP1 and RNP2, in addition to the combination paired gRNA and amplifier molecule, if present—currently HSV vectors are most useful. HSV shows tropism for a wide variety of cell types with high infectivity for both dividing and nondividing cells. Moreover, HSV expresses over eighty different genes, many of which are not essential for its replication cycle, HSV thus has the potential to carry a substantial payload, allowing the insertion of multiple transgenes. Finally, the latent HSV genome does not integrate into cellular DNA, but remains episomal as a closed circular molecule, thus avoiding the risks of insertional mutagenesis.

HSV amplicon vectors are minimal HSV vectors that rely on a full complement of helper virus functions for their production; however, HSV amplicon vectors stand out for their unparalleled payload capacity (~150 kb). Like other HSV vectors, amplicon vectors remain extrachromosomal and therefore pose no risk of insertional mutagenesis. HSV amplicon vectors essentially are regular HSV virions that possess the same properties as typical HSV-1 particles, including structure, tropism and immunogenicity, yet package a genome-length amplicon plasmid concatemer instead of a functional HSV genome. Standard amplicon plasmids comprise, e.g., an *E. coli* origin of replication (ColE1), an antibiotic resistance gene, a transgene expression cassette of up to 150 kb in size, a single HSV-1 origin of replication, and an HSV-1 cleavage/packaging signal. Due to the lack of viral protein-coding genes, amplicon life cycle and production are dependent on the presence of a helper virus typically a replication-defective HSV-1; complementing cells are then used to enable helper virus replication and amplicon replication and packaging.

EXAMPLES

The following examples are put forth so as to provide those of ordinary skill in the art with a complete disclosure and description of how to make and use the present invention and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I: RNP Formation

For RNP complex formation, 250 nM of LbCas12a nuclease protein was incubated with 375 nM of a target-specific gRNA in 1× Buffer (10 mM Tris-HCl, 100 µg/mL BSA) with 2-15 mM $MgCl_2$ at 25° C. for 20 minutes. The total reaction volume was 2 μL. Other ratios of LbCas12a nuclease to gRNAs were tested, including 1:1, 1:2 and 1:5. The incubation temperature ranged from 20° C.-37° C., and the incubation time ranged from 10 minutes to 4 hours.

Example II: gRNA Preparation gRNA oligonucleotides were amplified by PCR using the KAPA HIFI HOTSTART™ according to the manufacturer's protocol (Roche Sequencing Solutions, Indianapolis, IN USA). gRNAs were then synthesized through in vitro transcription using a T7 promoter with the NEB HIGH-SCRIBE™ T7 High Yield RNA synthesis kit according to the manufacturer's protocol (New England Biolabs, Ipswich, MA USA). Post transcription, the gRNAs were purified using RNAClean XP beads according to the manufacturer's protocol (Beckman Coulter, Brea, CA USA). The gRNAs were eluted from the beads in a hybridization buffer (50 mM $MgCl_2$, 10 mM Tris HCl, 50 mM NaCl) and gRNA concentration was measured on a nanodrop instrument.

Example III: In Vitro Trans-Cleavage Assay Using Combination Guide Nucleic Acids In vitro trans-cleavage of Cas13a and Cas12a was measured through cleavage of ssRNA-FAM (Cas13a in RNP1) and ssDNA-HEX (Cas12a in RNP2) probes. A mastermix containing all reagents below except for the combination guide nucleic acid ("combination gRNA") was created. The mastermix was added to a 96- or 384-well plate on ice. The gRNAs were subsequently added to wells containing the mastermix. The plates were read on a BioRad CFX Real-Time System™, incubating at 37° C., reading the plate every 2 minutes for a total 200x. The ssRNA probe sequence was/56-FAM/rUrU rUrUrU/3IABkFQ/ and the ssDNA probe sequence was/5HEX/TTATT/3IABkFQ/. The in vitro cleavage assay components are shown in Table 1:

TABLE 1

| Reagent | Final concentration (nM) |
|---|---|
| CUTSMART ® | 1X |
| LbCas12a | 100.00 |
| LwCas13a | 100.00 |
| Paired gRNA | 200.00 |
| GFP PCR Target (Cas12a target) | 6.70 |
| KRAS ssRNA target (Cas13a target) | 36.00 |
| FAM-ssRNA | 250.00 |
| HEX-ssDNA | 250.00 |

Example IV: In Vitro Trans-Cleavage Assay for Amplifiers/Single Blocked Guides

In vitro trans cleavage of Cas13a and Cas12a was measured through cleavage of ssRNA-FAM (Cas13a in RNP1) and ssDNA-HEX (Cas12a in RNP2) probes. Again, a mastermix containing all reagents below except for the Amplifier/single blocked GFP gRNA was created. The mastermix was added to a 96 or 384 well plate on ice. Amplifiers/single blocked GFP gRNAs were subsequently added to wells containing the mastermix. Plates were read on a BioRad CFX Real-Time System. The BioRad CFX Real-Time protocol included iIncubating at 37° C., reading the plate every 2 minutes for a total 200x. The ssRNA probe sequence was/56-FAM/rUrU rUrUrU/3IABkFQ/ and the ssDNA probe sequence was/5HEX/TTATT/3IABkFQ/. The in vitro cleavage assay components for amplifiers and single blocked guides are shown in Table 2:

TABLE 2

| Reagent | Final concentration (nM) |
|---|---|
| Cutsmart | 1X |
| LbCas12a | 100.00 |
| LwCas13a | 100.00 |
| Unblocked crKRAS/NT | 100.00 |
| Amplifier/blocked GFP gRNA | 100.00 |
| GFP PCR Target (Cas12a target) | 6.70 |
| KRAS ssRNA target (Cas13a target) | 36.00 |
| FAM-ssRNA | 250.00 |
| HEX-ssDNA | 250.00 |

Example V: In Vitro Cis-Cleavage Assay for Combination Guide Nucleic Acids, Amplifiers and Single Blocked GFP gRNAs Cis-cleavage by Cas12a was analyzed by measuring the fraction of cleaved GFP PCR target via qPCR. The product from the in vitro trans cleavage assay was used in the qPCR reaction and measured with the Bio-Rad CFX Real-Time System™ (Bio-Rad, Inc. Hercules, CA USA). The Thermo Fisher Scientific Protocol for qPCR (2× SYBR® Green PCR) was followed.

Example VI: In Vivo Nucleofections

HEK293T cells were washed with PBS, trypsinized to detach the cells from the plate, and DMEM media (10% FBS, with Penstrep) was added. Cells were counted and 2e5 cells per condition were nucleofected. The amounts of purified nuclease or amplifier, combination guide nucleic acids or single guide nucleic acids used in the nucleofections are shown in Table 3:

TABLE 3

| Reagent | Amount (pmol) |
|---|---|
| Lw Cas13a (GENSCRIPT ®) | 100 |
| LbCas12a (IDT) | 100 |
| Blocked combination guide nucleic acids | 200 |
| Unblocked combination guide nucleic acid | 80 |
| Amplifer | 100 |
| Single guide nucleic acid | 100 |

Example VII: Results

FIGS. 6A-6L show the experimental setup and results obtained for various experiments for screening combination paired gRNAs having different numbers of loops and differently-sized loops. The combination paired gRNAs comprise 1) a first gRNA (gRNA1) configured to complex with a first nucleic acid-guided nuclease and 2) a blocked second gRNA (gRNA2) configured to complex with a second nucleic acid-guided nuclease.

Figure 6A:
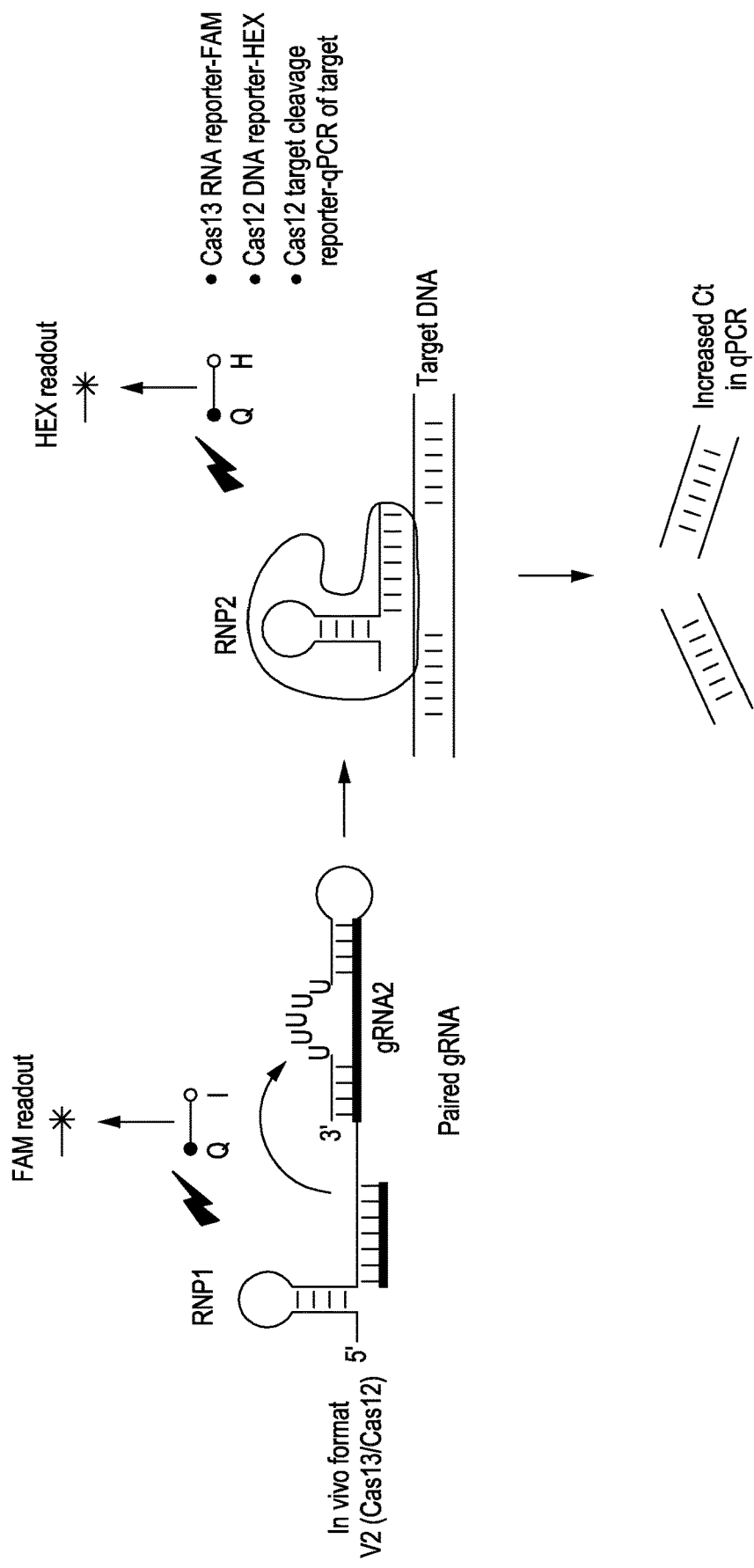
FIG. 6A is an illustration of the assay scheme used to generate the data reported in FIGS. 6D-6L.

FIG. 6A shows the assay format used in the experiments described below, with the exception of the experiment that generated the results in FIG. 6C. Here, there are two fluorescent readouts—FAM for an RNA reporter (ssRNA-FAM, Cas13 used in RNP1) and Hex for a DNA reporter (ssDNA-HEX, Cas12 used in RNP2)—as well as a qPCR readout for cleavage of the RNP2 target (GFP).

Figure 6B:
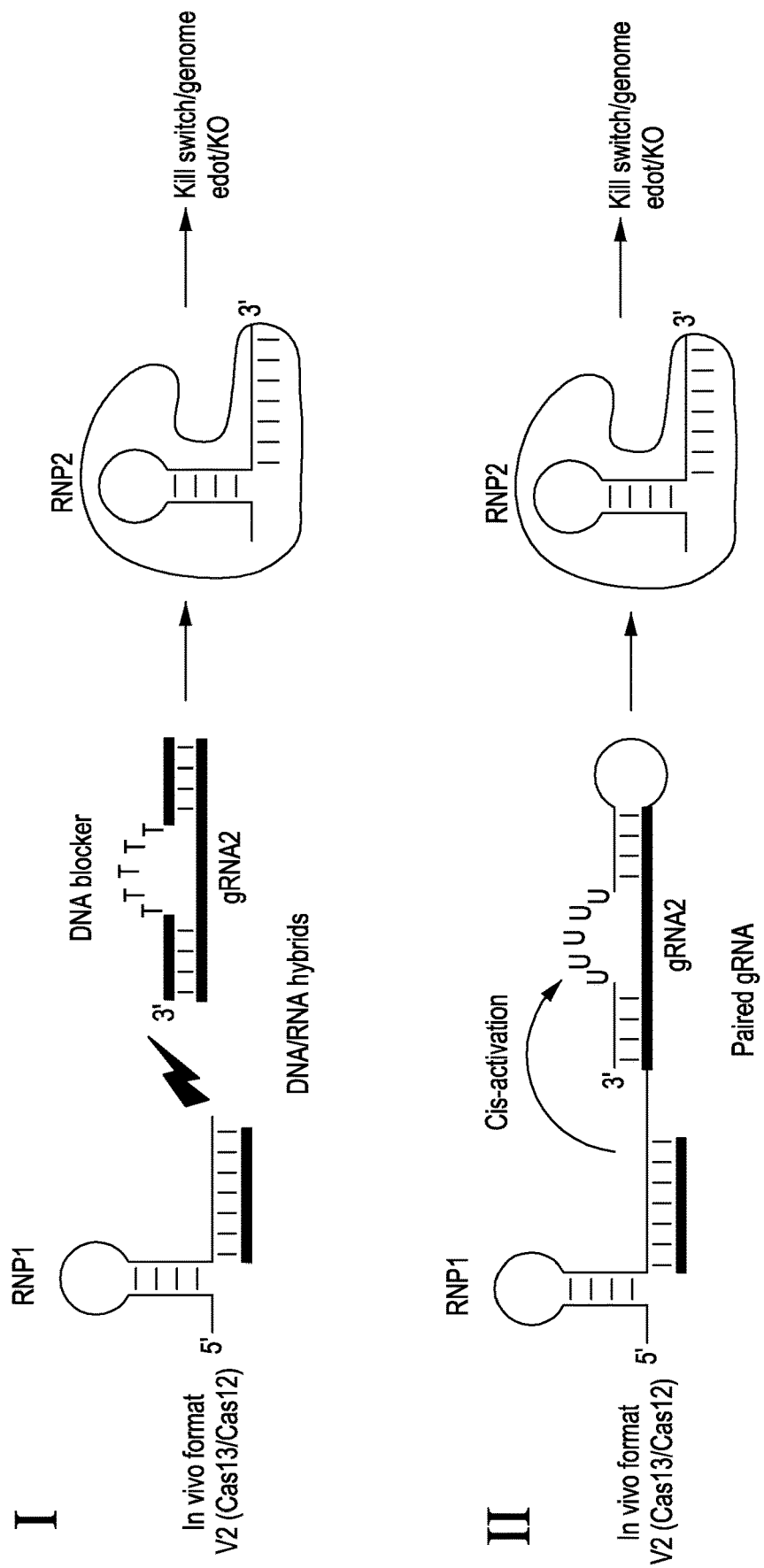
FIG. 6B is an illustration of two architectures of in vivo assays.

FIG. 6B shows two different experimental setups. I. First, there is a Cas12/Cas12 format with a hybrid gRNA2/DNA block that is not a combination paired gRNA, where the gRNA2 acts upon an effector such as a kill switch, genome edit, or knock out. II. Second is the Cas13/Cas12 format with a combination paired gRNA, where the gRNA2 acts upon an effector such as a kill switch, transcription enhancer, genome edit, or knock out. The combination paired gRNAs vary by the number and size of loops in the blocked gRNA2.

Figure 6C:
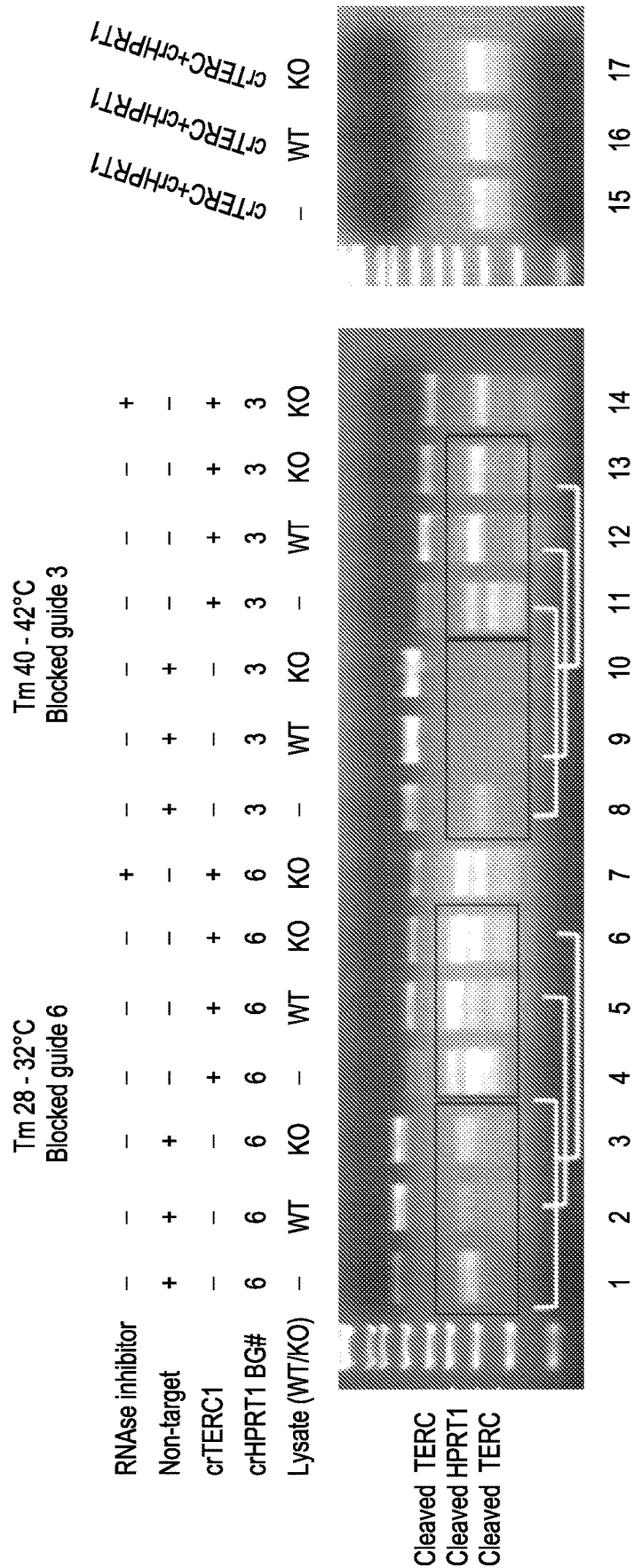
FIGS. 6C-6M show the results obtained from experiments performed using the Cascade assays according to certain embodiments.

In FIG. 6C, blocked DNA/RNA hybrid guides (shown in (I.) in FIG. 6B) were generated by hybridization of gRNA molecules with complementary DNA molecules in a 1:2 ratio. The blocked DNA/RNA hybrid guides were added to RNP1 containing reactions with PCR amplicons of the RNP1 target (TERC) and RNP2 target (HPRT1), with untreated samples on the right. Activity was assessed by agarose gel electrophoresis of the products following 2 hour incubations in the presence 1:10 V:V of the indicated cell lysates or an equivalent volume of water for the controls. The results show that addition of the RNP1 guide activates RNP2 in the absence of cell lysate (compare lane 1 to lane 4 for guide 6 and lane 8 and lane 11 for guide 3). The cascade is abrogated in the presence of HEK293T (WT) cell lysate (compare lane 2 to lane 5 for guide 6 and lane 9 and lane 12 for guide 3). Partial rescue of the full cascade is seen in the presence of cell lysates from a ΔRnase H cell line (compare lane 3 to lane 6 for guide 6 and lane 10 and lane 13 for guide 3).

Figure 6D:
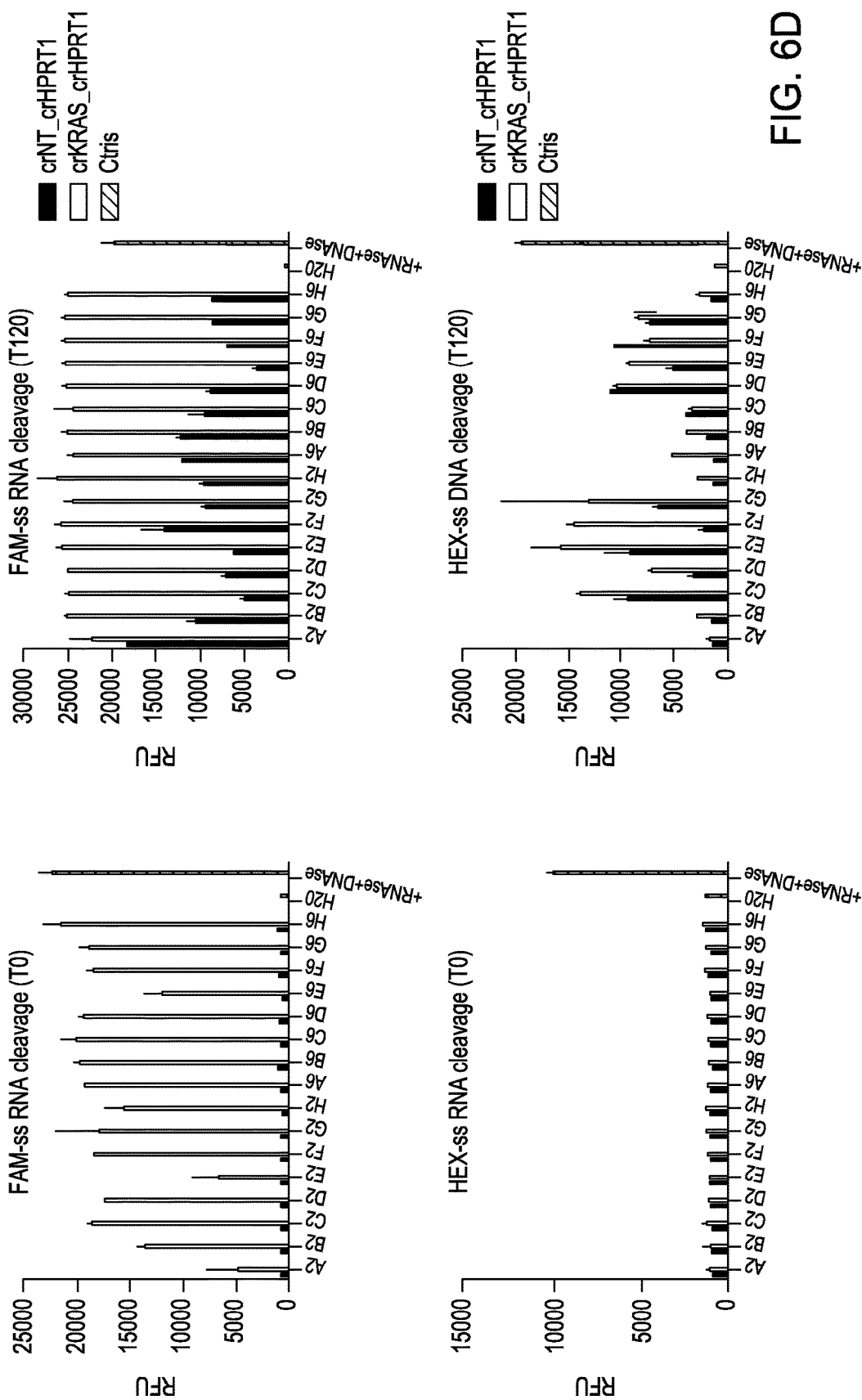

In FIG. 6D the assay system shown in FIG. 6A was employed, using single-loop combination paired gRNAs. The assay conditions recited in Example IV were used, except that an HPRT1 PCR target was used rather than a GFP PCR Target. Note that cleavage of the ssRNA-FAM probe at T0 was almost immediate in the samples with the crKRAS_crHPRT1 combination paired gRNAs but not with the cr non-targeting gRNAs, although some signal did appear from the cr non-targeting gRNAs at T120. Cleavage of the ssDNA-HEX probe (evidence of RNP2 trans-cleavage activity) was low at T0 but was high in some samples at T120.

In FIGS. 6E-6L, the assay system shown in FIG. 6A was employed, with 34 different combination paired gRNAs comprising a first gRNA (gRNA1) with the crRNA configured to complex with LwCas13a and a non-targeting spacer or a KRAS-targeting spacer and a blocked second gRNA (gRNA2) with the crRNA configured to complex with LbCas12a and GFP-targeting spacer when unblocked. In addition, fifteen different amplifier molecules were tested. Again, two fluorescent readouts—FAM for an RNA reporter (ssRNA-FAM, Cas13 used in RNP1) and Hex for a DNA reporter (ssDNA-HEX, Cas12 used in RNP2) were used—as was a qPCR readout for cleavage of the RNP2 target (GFP).

Figure 6E:
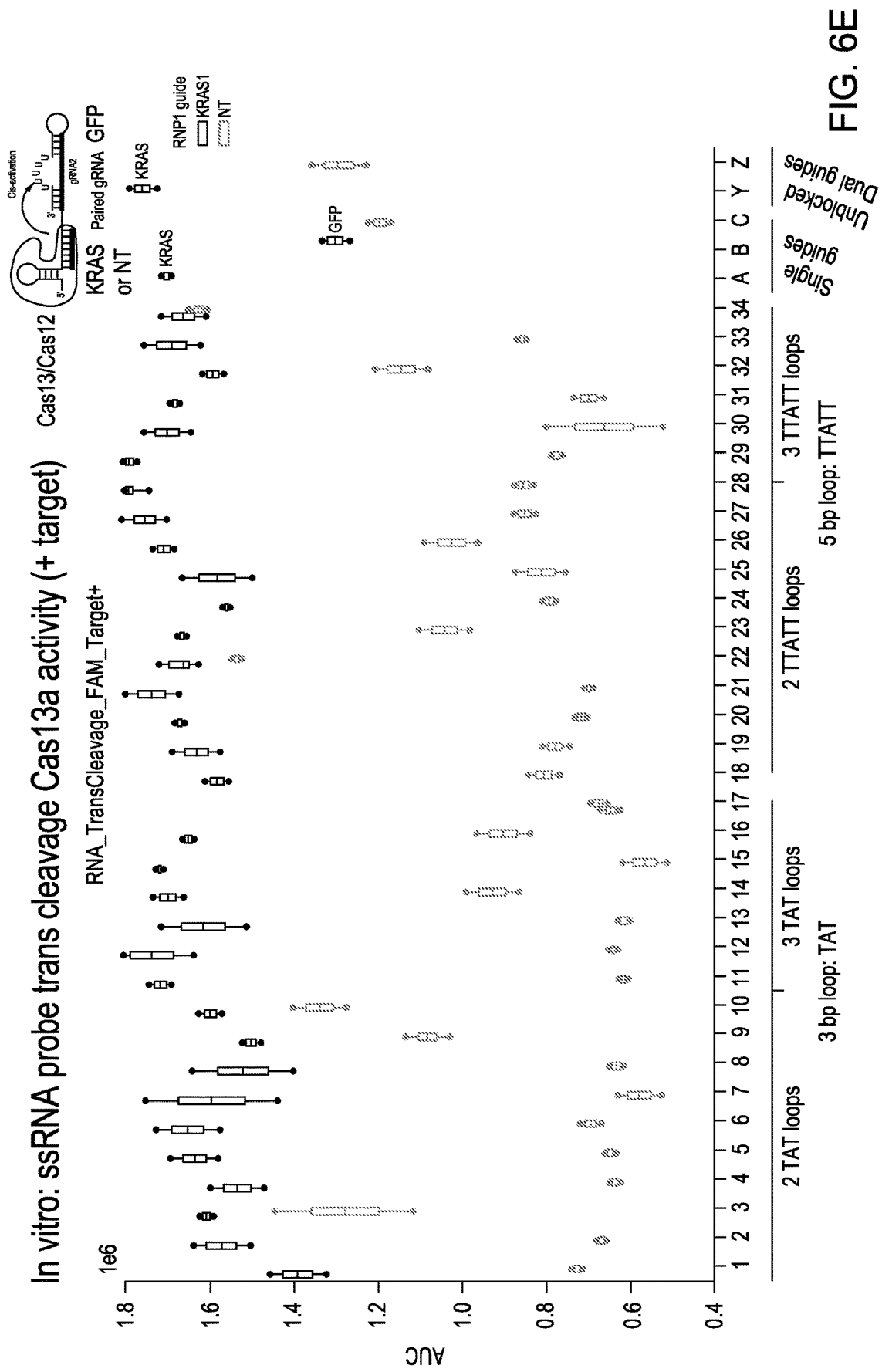

In FIG. 6E, the 34 different combination paired gRNAs were screened in an in vitro assay with a KRAS target nucleic acid of interest. The results demonstrate ssRNA-probe cleavage with the KRAS combination paired gRNA in the presence of Cas13a crRNA target and low activity of the non-target combination paired gRNAs. That is, trans-cleavage activity of RNP1 is demonstrated. A, B and C indicate single guide controls and Y and Z are combination paired gRNAs where the gRNA2 (for GFP) is unblocked.

Figure 6F:
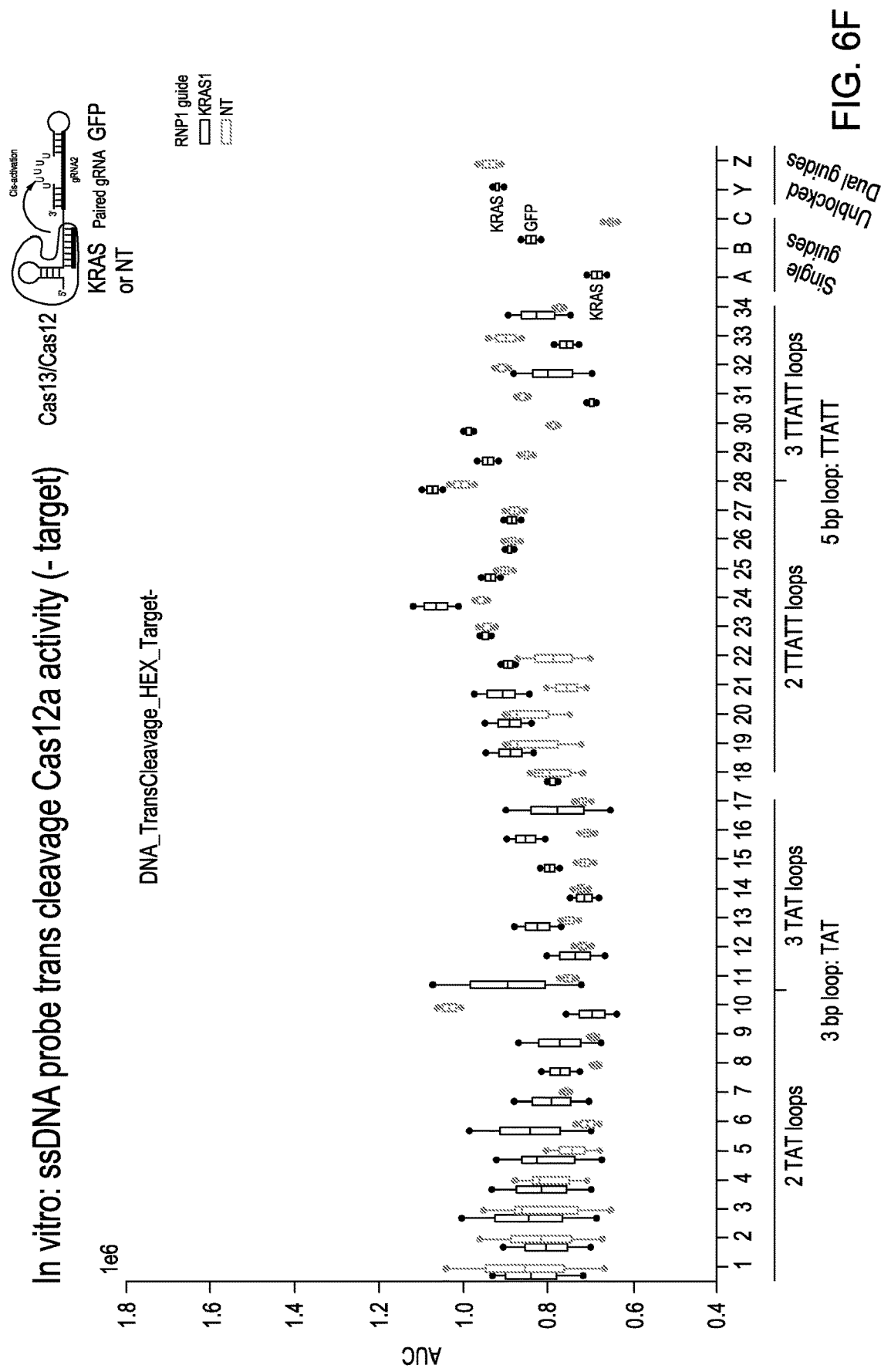
Figure 6G:
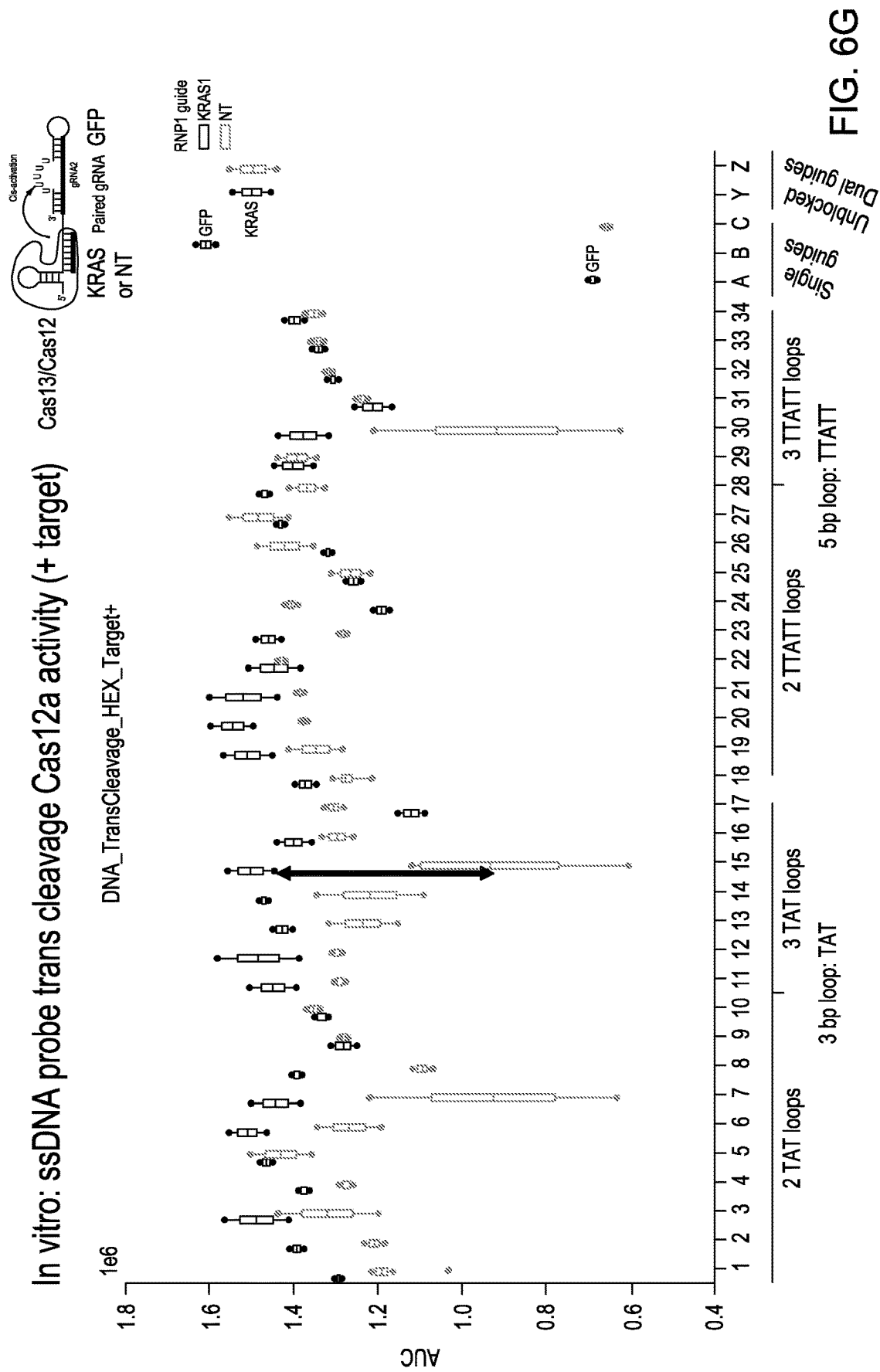

In FIG. 6F, the same 34 different combination paired gRNAs were screened in an in vitro assay for trans-cleavage in the absence of KRAS target. The results demonstrate that there is little to no trans-cleavage of the ssRNA reporter in the absence of the KRAS target nucleic acid of interest. A, B and C indicate single guide controls and Y and Z are combination paired gRNAs where the gRNA2 (for GFP) is unblocked.

In FIG. 6G, again the 34 combination paired gRNAs were screened in an in vitro assay with a KRAS target nucleic acid of interest. The results demonstrate that in some samples, there is ssDNA-probe cleavage with the KRAS combination paired gRNA in the presence of Cas12a crRNA target (GFP) and low activity of the non-target combination paired gRNAs. A, B and C indicate single guide controls and Y and Z are combination paired gRNAs where the gRNA2 (for GFP) is unblocked.

Figure 6H:
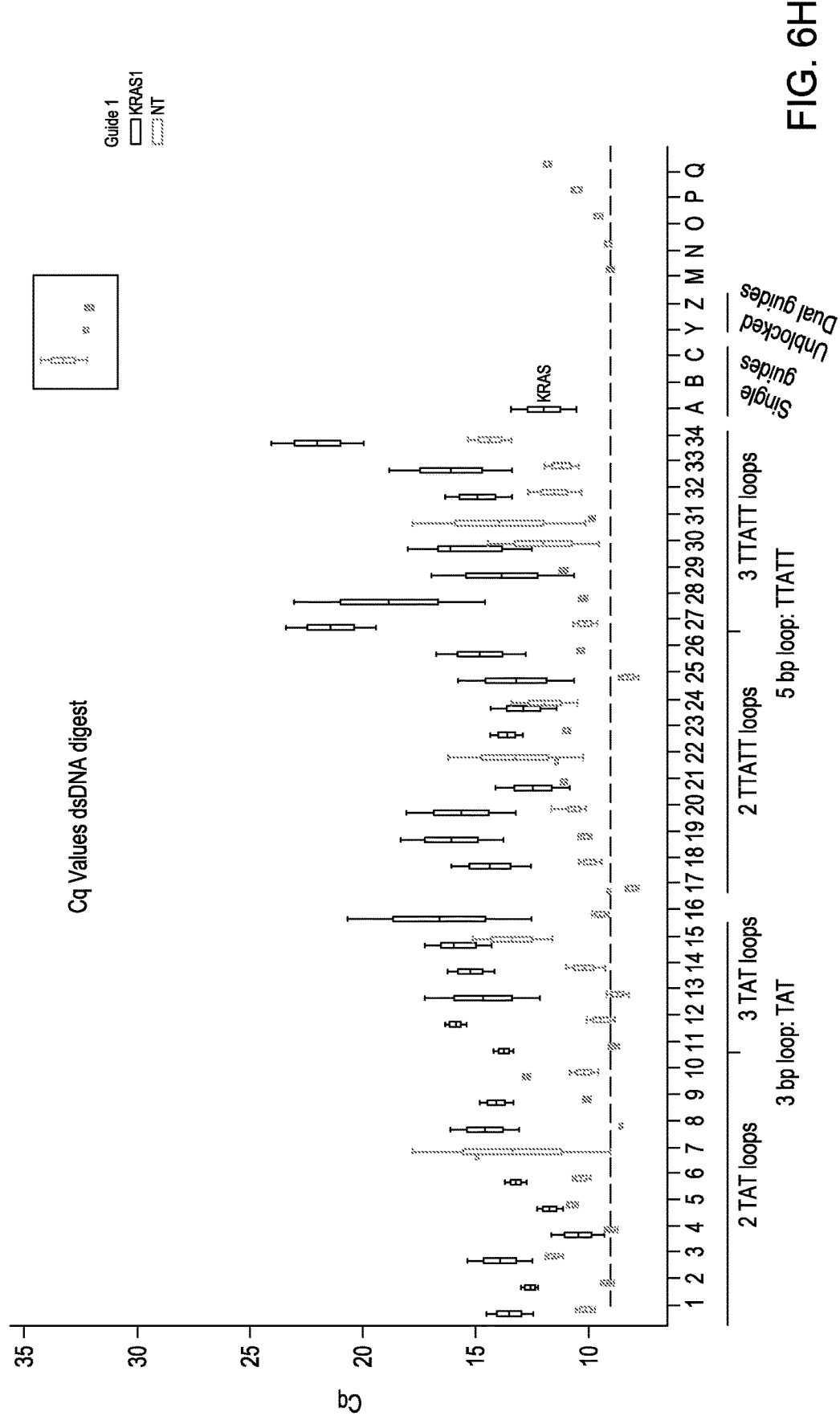

The results shown in FIG. 6H are an in vitro proxy for cleavage of a final therapeutic target (i.e., signal transduction), as cis-cleavage is a more direct readout of Cas12a nuclease activity (nuclease activity by RNP2). Higher Cq values indicate a greater digestion of the RNP2 target (GFP); that is, the KRAS-GFP combination paired gRNAs are unblocking and causing cis-cleavage of GFP target more than the non-targeting-GFP combination paired gRNAs in most designs. The Cq scale is logarithmic.

Figure 6I:
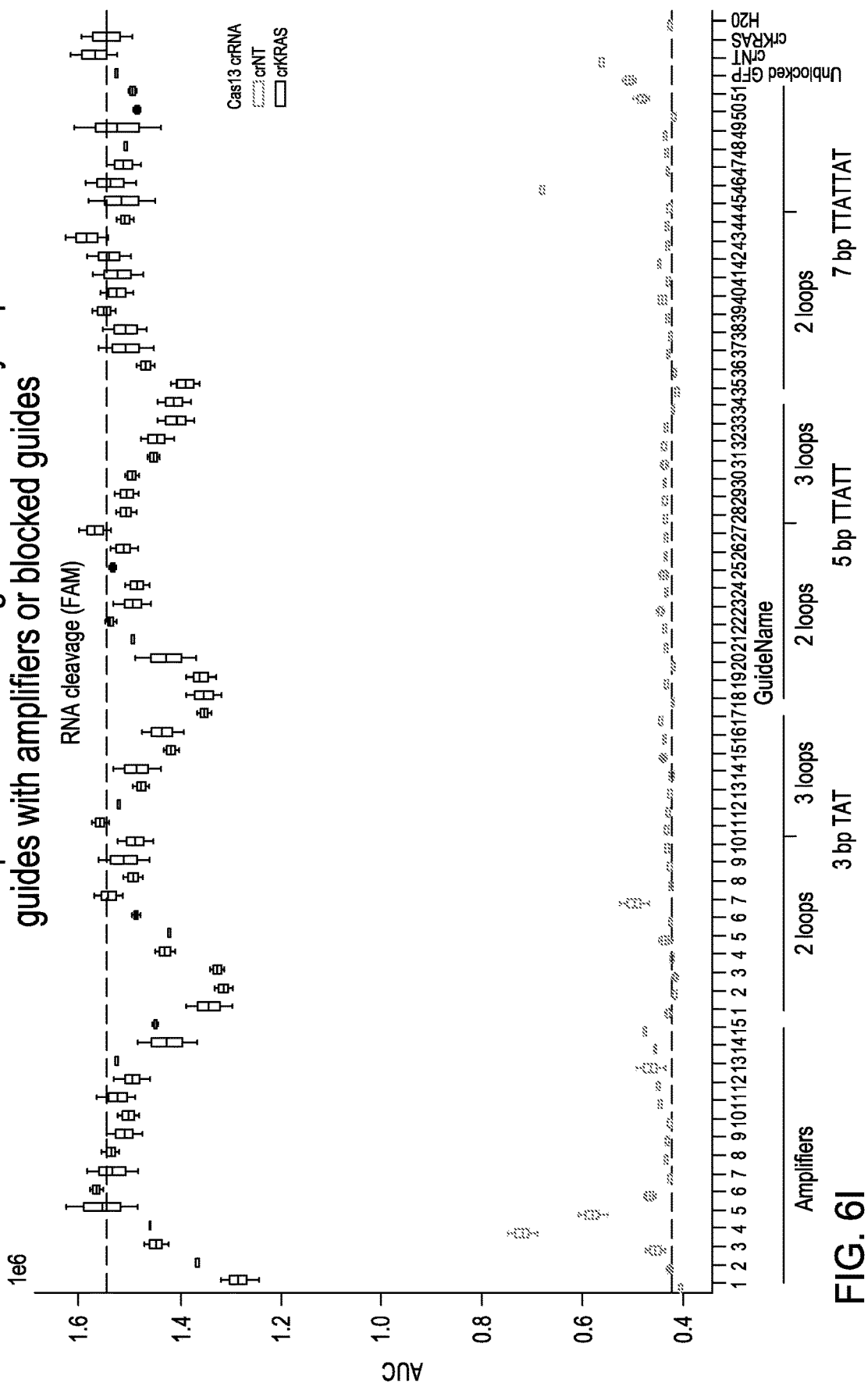

In FIG. 6I, fifteen different amplifiers and single gRNA2 blocked guides (single GFP guides—i.e., not combination paired gRNAs) were used in an in vitro assay with RNP1s comprising a non-targeting guide or a KRAS targeting guide. In this experiment, the single blocked guides comprised 2 or 3 loops, of 3 basepairs, 5 basepairs, or 7 basepairs in size. The results obtained demonstrate that KRAS mRNA activates Cas13 trans-cleavage.

Figure 6J:
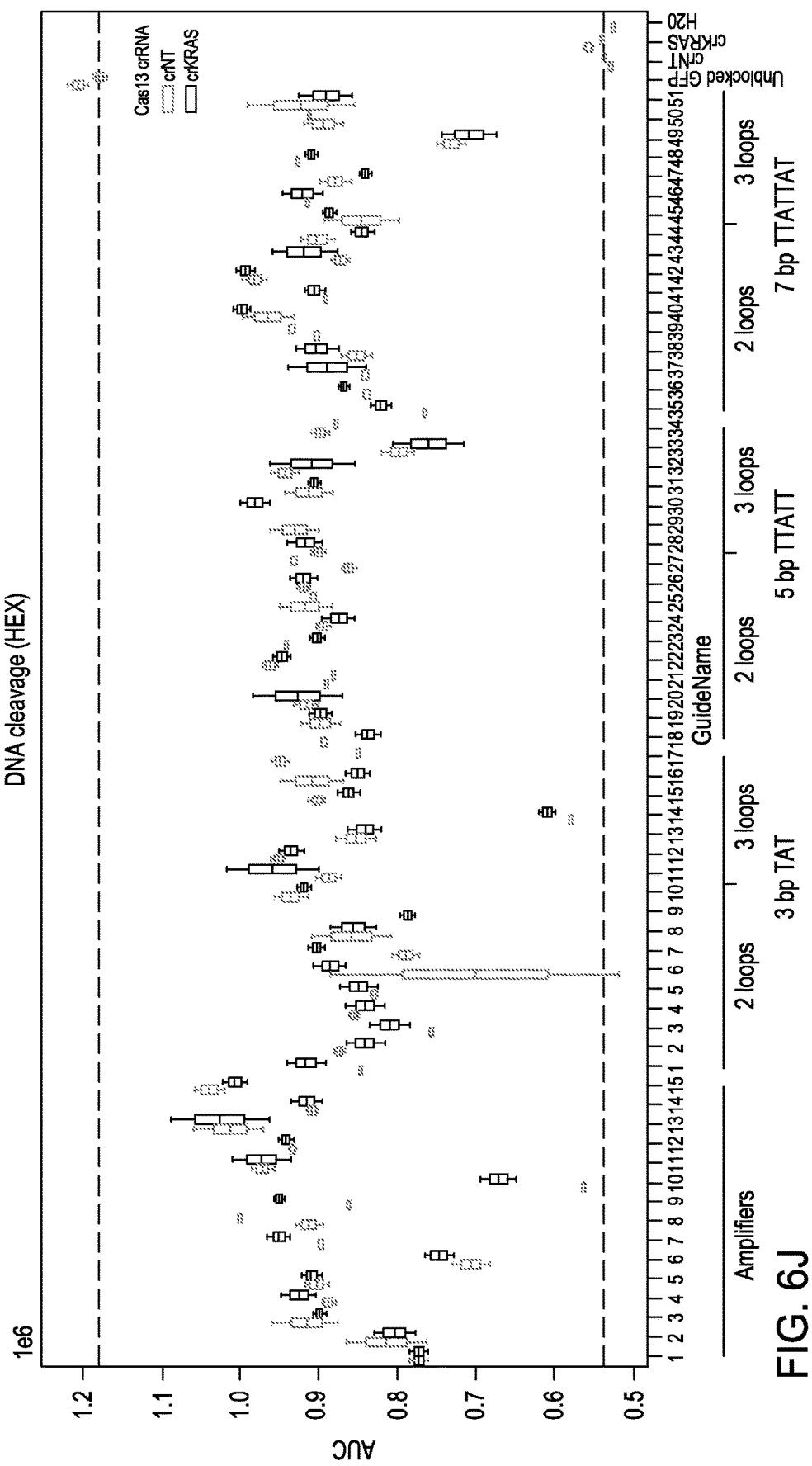

FIG. 6J, like FIG. 6I, employed fifteen different amplifiers and single gRNA2 blocked guides (GFP guides) in an in vitro assay with RNP1s comprising a non-targeting guide or a KRAS targeting guide. In this experiment, the single blocked guides comprised 2 or 3 loops, of 3 basepairs, 5 basepairs, or 7 basepairs in size. Note that there are greater values in samples comprising the KRAS targeting guides relative to the non-targeting guides; however, the single guides do not appear to work as well as the combination paired gRNAs.

Figure 6K:
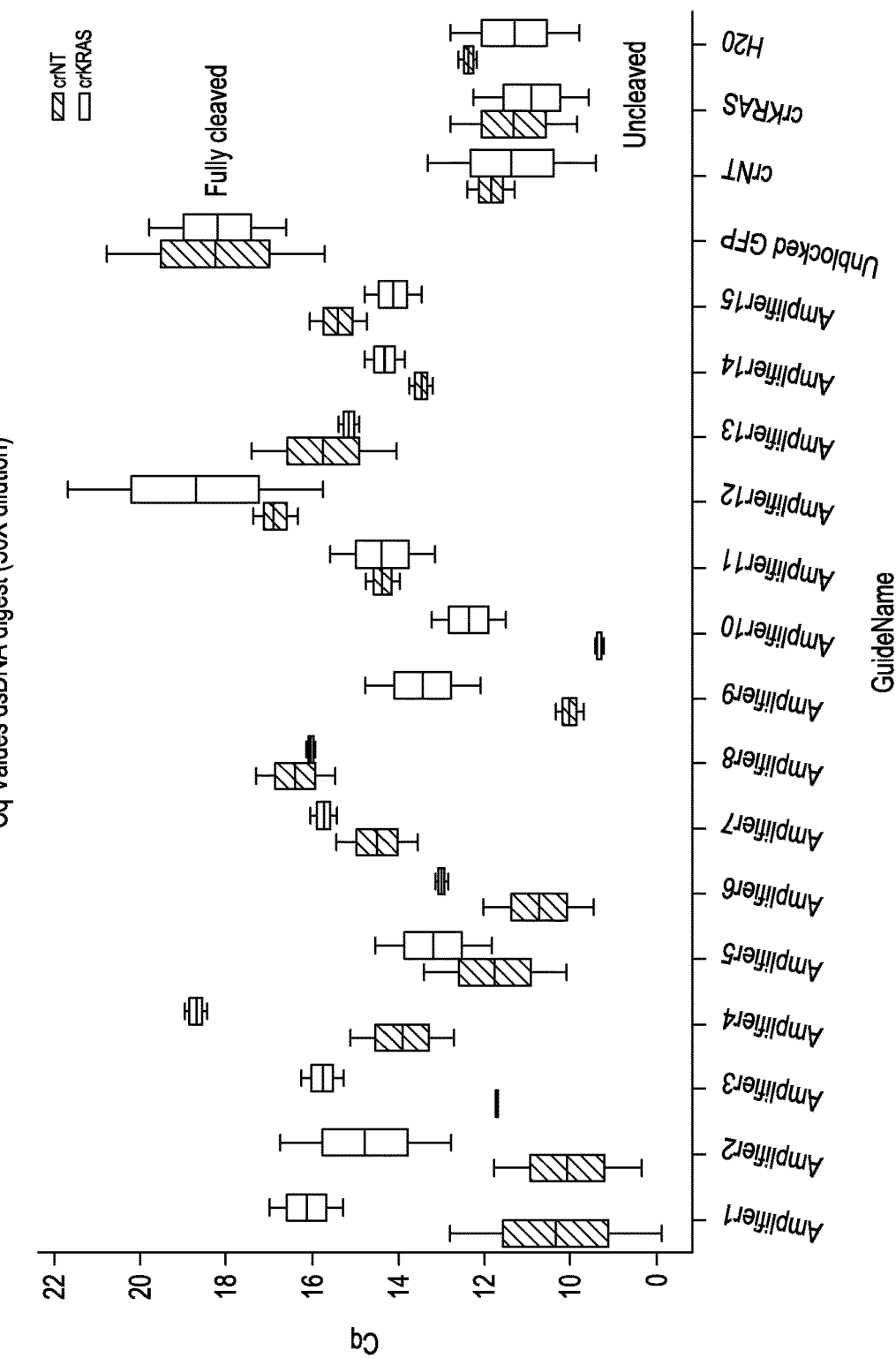

The results in FIG. 6K are an in vitro proxy for cleavage of a final in vivo therapeutic target (i.e., signal transduction), showing Cas13 triggering of Cas12 cis-cleavage (looking at the differences between points for each amplifier). The higher Cq values indicate a greater digestion of the RNP2 target. For amplifier 1, the crNT value of 11 is $2^5$-fold lower than the crKRAS value of 16; that is, there is $2^5$-fold less intact DNA with crKRAS. The Cq scale is logarithmic.

Figure 6L:
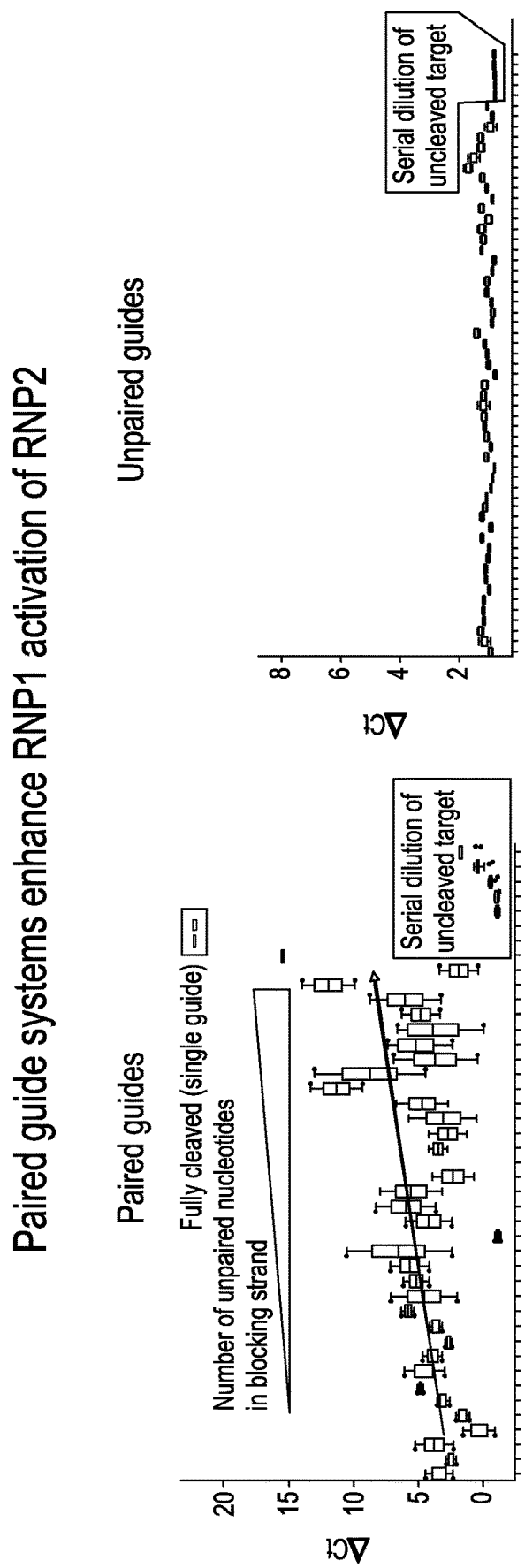

FIG. 6L demonstrates that combination paired gRNAs enhance RNP1 activation of RNP2, while there is very little activity with unpaired gRNAs; further, RNP1 activation is correlated with the total number of unpaired nucleotides (i.e., number of loops and/or number of nucleotides in the loops) in the blocking strand. Here there is a comparison of the difference in Ct values of KRAS-GFP paired guides to the NT-GFP paired guides, where a higher Ct value indicates that the KRAS-GFP guide is more active than the NT-GFP guide (i.e., getting more Cas12a crRNA target cleavage). The serial dilution of uncleaved target is included to try to gauge the fraction of cleaved dsDNA target. Theoretically the 32× crNT sample (X-axis far right) would have ~6% target left.

Figure 6M:
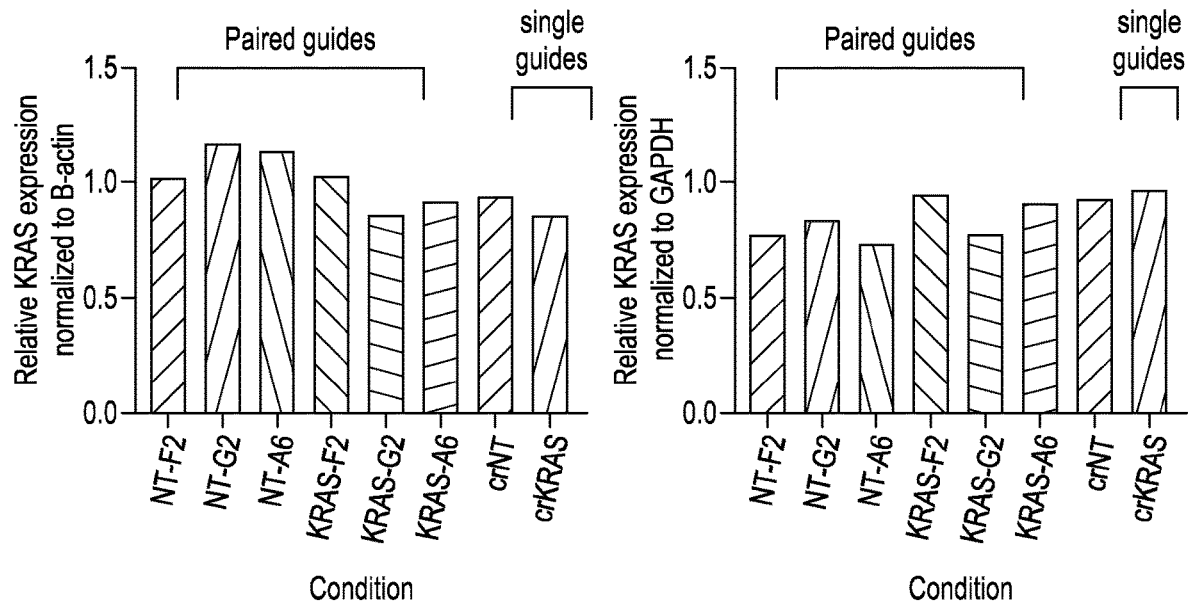
Figure 6M:
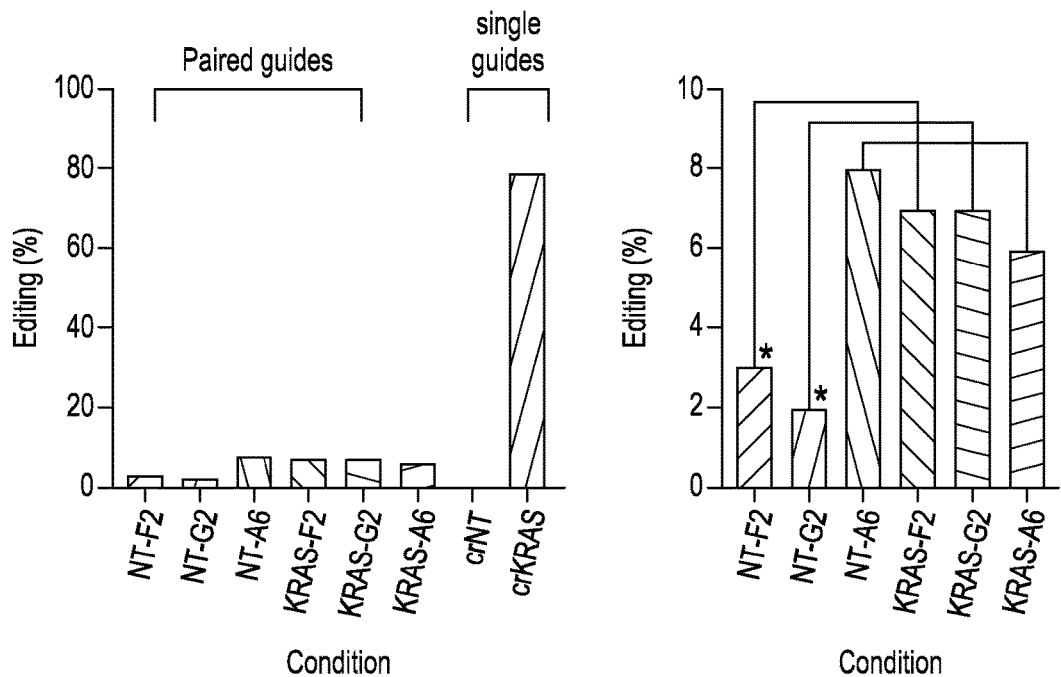

FIG. 6M shows the results of in vivo editing of combination paired guides with KRAS-targeting gRNA1 and HPRT1-targeting gRNA2. Although the knockdown of KRAS does not appear to be high compared to the single guides or to the non-targeting combination paired guides, HPRT1 editing is higher (see the bar graph at bottom right).

While certain embodiments have been described, these embodiments have been presented by way of example only and are not intended to limit the scope of the present disclosures. Indeed, the novel methods, apparatuses, modules, instruments and systems described herein can be embodied in a variety of other forms; furthermore, various omissions, substitutions and changes in the form of the methods, apparatuses, modules, instruments and systems described herein can be made without departing from the spirit of the present disclosures. The accompanying claims and their equivalents are intended to cover such forms or modifications as would fall within the scope and spirit of the present disclosures.

We claim:

1. A method for activating an effector nucleic acid in vivo in a cell comprising the steps of:
   providing cascade system components, wherein the cascade system components comprise:
      a plurality of combination guide nucleic acids, wherein each combination guide nucleic acid comprises 1) a first guide nucleic acid portion comprising a region that binds to a first nucleic acid-guided nuclease to form a first ribonucleoprotein complex and a region complementary to a target nucleic acid of interest coupled by a linker to 2) a blocked second guide nucleic acid portion comprising a) a region that binds to a second nucleic acid-guided nuclease, b) a region complementary to an effector nucleic acid, c) regions of complementarity to the region complementary to the effector nucleic acid forming clamp sequences, and d) regions of non-complementarity to the region complementary to the effector nucleic acid, wherein at least one of the regions of non-complementarity forms at least one loop, and wherein the blocked second guide nucleic acid portion initially is blocked and unable to bind the effector nucleic acid or form a second ribonucleoprotein complex with the second nucleic acid-guided nuclease; and
      the first and second nucleic acid-guided nucleases, wherein the first and second nucleic acid-guided nuclease are Type V or Type VI nucleic acid-guided nucleases that exhibit both cis- and trans-cleavage activity;
   delivering the cascade system components to cells under conditions that allow the target nucleic acids of interest in the cells, if present, to bind to the first ribonucleoprotein complex, wherein upon binding of the target nucleic acid of interest to the first ribonucleoprotein complex the first ribonucleoprotein complex becomes active initiating trans-cleavage activity of the first ribonucleoprotein complex thereby cleaving the blocked second guide nucleic acid portion from the combination guide nucleic acid and unblocking the blocked second guide nucleic acid portion producing at least one unblocked second guide nucleic acid, and wherein the at least one unblocked second guide nucleic acid forms a second ribonucleoprotein complex with the second nucleic acid-guided nuclease and is able to bind to and activate the effector nucleic acid in the cell.

2. The method of claim 1, wherein the first guide nucleic acid portion of the combination guide nucleic acid is approximately 63 to 70 nucleotides in length.

3. The method of claim 1, wherein the linker of the combination guide nucleic acid is approximately 5-50 nucleotides in length.

4. The method of claim 3, wherein the linker of the combination guide nucleic acid is approximately 10-40 nucleotides in length.

5. The method of claim 4, wherein the linker of the combination guide nucleic acid is approximately 10-20 nucleotides in length.

6. The method of claim 5, wherein the linker of the combination guide nucleic acid is single-stranded.

7. The method of claim 1, wherein the at least one loop comprises 3-10 nucleotides.

8. The method of claim 7, wherein the at least one loop comprises 3 nucleotides.

9. The method of claim 7, wherein the at least one loop comprises 5 nucleotides.

10. The method of claim 7, wherein the at least one loop comprises 7 nucleotides.

11. The method of claim 1, wherein the regions of non-complementarity form two loops.

12. The method of claim 11, wherein the two loops each comprise 3-10 nucleotides.

13. The method of claim 12, wherein at least one of the two loops comprises 3 nucleotides.

14. The method of claim 12, wherein at least one of the two loops comprises 5 nucleotides.

15. The method of claim 12, wherein at least one of the two loops comprises 7 nucleotides.

16. The method of claim 1, wherein the regions of non-complementarity form three loops.

17. The method of claim 16, wherein the three loops each comprise 3-10 nucleotides.

18. The method of claim 17, wherein at least one of the three loops comprises 3 nucleotides.

19. The method of claim 17, wherein at least one of the three loops comprises 5 nucleotides.

20. The method of claim 17, wherein at least one of the three loops comprises 7 nucleotides.

21. The method of claim 1, wherein there are two loops and the loops are different sizes.

22. The method of claim 1, wherein there are three loops and the loops are all different sizes.

23. The method of claim 1, wherein the first guide nucleic acid portion binds to the Type VI RNA-guided RNA endonuclease and the blocked second guide nucleic acid portion binds to the Type V RNA-guided DNA endonuclease.

24. The method of claim 1, wherein the first guide nucleic acid portion binds to the Type V RNA-guided DNA endonuclease and the blocked second guide nucleic acid portion binds to the Type VI RNA-guided RNA endonuclease.

25. The method of claim 1, wherein the first guide nucleic acid portion and the blocked second guide nucleic acid portion binds to the Type VI RNA-guided RNA endonuclease.

26. The method of claim 1, wherein the first guide nucleic acid portion and the blocked second guide nucleic acid portion binds to the Type V RNA-guided DNA endonuclease.

27. The method of claim 1, further comprising a hairpin loop formed at the end of a clamp sequence.

28. The method of claim 1, comprising at least two different combination guide nucleic acid molecules, wherein different combination guide nucleic acid molecules comprise different first guide nucleic acid portions that detect different target nucleic acids of interest and wherein different combination guide nucleic acid portions comprise different second guide nucleic acid sequences that activate different effector nucleic acids.

29. The method of claim 1, comprising at least two different combination guide nucleic acid molecules, wherein different combination guide nucleic acid molecules comprise different first guide nucleic acid portions that detect different target nucleic acids of interest and wherein different combination guide nucleic acid portions comprise the same second guide nucleic acid sequences that the activate same effector nucleic acids.

30. The method of claim 1, wherein the effector nucleic acid, when activated, acts upon an effector target.

* * * * *